United States Patent
Sapozhnikov et al.

(10) Patent No.: US 9,743,909 B1
(45) Date of Patent: Aug. 29, 2017

(54) IMAGING BUBBLES IN A MEDIUM

(71) Applicant: University of Washington through its Center for Commercialization, Seattle, WA (US)

(72) Inventors: Oleg A. Sapozhnikov, Seattle, WA (US); Michael R. Bailey, Seattle, WA (US); Joo Ha Hwang, Bellevue, WA (US); Tatiana D. Khokhlova, Seattle, WA (US); Vera Khokhlova, Seattle, WA (US); Matthew O'Donnell, Seattle, WA (US); Tong Li, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 268 days.

(21) Appl. No.: 14/278,197

(22) Filed: May 15, 2014

Related U.S. Application Data

(60) Provisional application No. 61/823,658, filed on May 15, 2013, provisional application No. 61/974,897, filed on Apr. 3, 2014.

(51) Int. Cl.
*A61N 7/02* (2006.01)
*A61B 8/08* (2006.01)
(Continued)

(52) U.S. Cl.
CPC ............ *A61B 8/481* (2013.01); *A61B 5/0062* (2013.01); *A61B 5/0507* (2013.01)

(58) Field of Classification Search
CPC ............ A61B 17/225; A61B 17/22004; A61B 17/2258; A61B 18/26; A61B 2017/00172;
(Continued)

(56) References Cited

U.S. PATENT DOCUMENTS 4,907,572 A   3/1990   Borodulin et al.
4,962,754 A   10/1990  Okazaki
(Continued)

FOREIGN PATENT DOCUMENTS

WO   2006060492   1/2006

OTHER PUBLICATIONS

Shabana, et al. (2009) "Comparison between color Doppler twinkling artifact and acoustic shadowing for renal calculus detection: an in vitro study," Ultrasound in Medicine and Biology, 35(2): 339-350.
(Continued)

*Primary Examiner* — Elmer Chao
(74) *Attorney, Agent, or Firm* — Christensen O'Connor Johnson Kindness PLLC

(57) ABSTRACT

A method for imaging a cavitation bubble includes producing a vibratory wave that induces a cavitation bubble in a medium, producing one or more detection waves directed toward the induced cavitation bubble, receiving one or more reflection waves, identifying a change in one or more characteristics of the induced cavitation bubble, and generating an image of the induced cavitation bubble using a computing device on the basis of the identified change in the one or more characteristics. The one or more received reflection waves correspond to at least one of the one or more produced detection waves reflection from the induced cavitation bubble. The identified change in one or more characteristics corresponds to the one or more received reflection waves.

12 Claims, 15 Drawing Sheets

(51) Int. Cl.
  *A61B 5/05* (2006.01)
  *A61B 5/00* (2006.01)
(58) Field of Classification Search
  CPC ........... A61B 2017/22088; A61B 2017/22089;
                  A61M 37/0092; A61N 7/00
  See application file for complete search history.

(56) References Cited

U.S. PATENT DOCUMENTS

| | | |
|---|---|---|
| 5,048,527 A | 9/1991 | Okazaki |
| 5,059,200 A | 10/1991 | Tulip |
| 5,065,763 A | 11/1991 | Green et al. |
| 5,240,005 A | 8/1993 | Viebach |
| 5,425,366 A | 6/1995 | Reinhardt et al. |
| 6,123,679 A | 9/2000 | Lafaut et al. |
| 6,206,843 B1 | 3/2001 | Iger et al. |
| 6,221,018 B1* | 4/2001 | Ramamurthy ......... A61B 8/481 600/443 |
| 6,385,474 B1 | 5/2002 | Rather et al. |
| 6,716,184 B2 | 4/2004 | Vaezy et al. |
| 6,728,567 B2 | 4/2004 | Rather et al. |
| 7,273,458 B2 | 9/2007 | Prausnitz et al. |
| 7,456,019 B2 | 11/2008 | Goodwin et al. |
| 7,485,101 B1 | 2/2009 | Faragalla |
| 8,038,616 B2 | 10/2011 | Angelsen et al. |
| 8,057,408 B2 | 11/2011 | Cain et al. |
| 2002/0065466 A1 | 5/2002 | Rather et al. |
| 2003/0028111 A1 | 2/2003 | Vaezy et al. |
| 2003/0204141 A1* | 10/2003 | Nock ................ A61M 37/0092 600/439 |
| 2004/0006288 A1 | 1/2004 | Spector |
| 2004/0024315 A1 | 2/2004 | Chalana et al. |
| 2004/0059265 A1 | 3/2004 | Candy et al. |
| 2004/0059319 A1 | 3/2004 | Bohris |
| 2006/0052699 A1 | 3/2006 | Angelsen et al. |
| 2006/0240550 A1 | 10/2006 | Goodwin et al. |
| 2008/0091125 A1 | 4/2008 | Owen et al. |
| 2008/0146908 A1 | 6/2008 | Wu |
| 2008/0319356 A1* | 12/2008 | Cain ................ A61B 17/22004 601/2 |
| 2009/0227992 A1 | 9/2009 | Nir |
| 2009/0230822 A1 | 9/2009 | Kushculey et al. |
| 2009/0264754 A1* | 10/2009 | Dahl .................... A61B 8/0875 600/438 |
| 2009/0275866 A1 | 11/2009 | Gelbart |
| 2009/0292204 A1* | 11/2009 | Pansky ................ A61B 5/6851 600/439 |
| 2009/0299187 A1 | 12/2009 | Bailey et al. |
| 2010/0056924 A1* | 3/2010 | Powers .................. A61B 8/481 600/458 |
| 2010/0256534 A1 | 10/2010 | Lacoste et al. |
| 2011/0251528 A1* | 10/2011 | Canney ................... A61N 7/02 601/3 |
| 2011/0263967 A1 | 10/2011 | Bailey et al. |
| 2013/0072854 A1* | 3/2013 | Mohan ............... A61K 41/0028 604/22 |
| 2013/0303906 A1 | 11/2013 | Cain et al. |

OTHER PUBLICATIONS

Rosenschein, et al. (2000) "Ultrasound imaging-guided noninvasive ultrasound thrombolysis: preclinical results," Circulation, 10 2(2): 238-245.

Albala, et al.: Lower Pole 1: A Prospective Randomized Trial of Extracorporeal Shock Wave Lithotripsy and Nephrostolithotomy for Lower Pole Nephrolithiasis—Initial Results. The Journal of Urology, 166: 2072, 2001.

Pearle, et al: Prospective Randomized Trial Comparing Shock Wave Lithotripsy and Ureteroscopy for Lower Pole Caliceal Calculi 1 cm or Less. The Journal of Urology, 179: S69, 2008.

Chen, et al.: Extracorporeal Shock Wave Lithotripsy for Lower Pole Calculi: Long-term Radiographic and Clinical Outcome. The Journal of Urology, 156: 1572, 1996.

Sampaio, et al.: Limitations of extracorporeal shockwave lithotripsy for lower caliceal stones: anatomic insight. J Endourol, 8:241, 1994.

Chiong, et al.: Randomized controlled study of mechanical percussion, diuresis, and inversion therapy to assist passage of lower pole renal calculi after shock wave lithotripsy. Urology, 65: 1070, 2005.

Kekre, et al.: Optimizing the fragmentation and clearance after shock wave lithotripsy. Curr Opin Urol, 18: 205, 2008.

Pace, et al.: Mechanical percussion, inversion and diuresis for residual lower pole fragments after shock wave lithotripsy: a prospective, single blind, randomized controlled trial. J Urol, 166: 2065, 2001.

International Search Report for PCT/US2011/033652, mailed Dec. 12, 2011.

Krings, et al., "Extracorporeal Shock Wave Lithotripsy Retreatment ("Stir-Up") Promotes Discharge of Persistent Caliceal Stone Fragments After Primary Extracorporeal Shock Wave Lithotripsy", The Journal of Urology, 1992, vol. 148, 1040-1042.

Parr, et al., "Does Further Extracorporeal Lithotripsy Promote Clearance of Small Residual Fragments?", British Journal of Urology, 1991, 68, 565-567.

Shah, et al., "Novel ultrasound method to reposition kidney stones", Ural Res, 2010, 38:491-495.

O'Brien, Jr. et al, The Risk of Exposure to Diagnostic Ultrasound in Postnatal Subjects Thermal Effects, J Ultrasound Med, 2008, 517-535, 27.

Heimdal, Ultrasound Doppler Measurements of Low Velocity Blood Flow: Limitations Due to Clutter Signals from Vibrating Muscles, IEEE Transaction Ultrasonics Ferroelectronics, and Frequency Control, 1997, pp. 873-881, vol. 44.

Jensen, Stationary Echo Canceling in Velocity Estimation by Time-Domain Cross-Correlation, IEEE Transactions on Medical Imaging, No. 3, 1993, pp. 471-477, vol. 12.

Chelfouh, et al., "Characterization of Urinary Calculi", AJR: 171, Oct. 1998, pp. 1055-1060.

Khan, et al., "Twinkling Artifact on Ineracerebral Color Doppler Sonography", AJNR Am J. Neuroradiol 20: Feb. 1999, pp. 246-247.

Kim, et al., "Color Doppler Twinkling Artifacts in Various Conditions During Abdominal and Pelvic Sonography", J Ultrasound Med, 2010, vol. 29, pp. 621-632.

Riccabona, Michael, "Potential of Modern Sonographic Techniques in Paediatric Uroradiology", European Journal of Radiology 43, 2002, pp. 110-121.

* cited by examiner

IMAGING BUBBLES IN A MEDIUM

CROSS-REFERENCE TO RELATED APPLICATIONS

This application claims priority to: (1) U.S. Provisional Patent App. No. 61/823,658, entitled "Method of detecting microbubbles in tissue and tissue phantoms using 'twinkling' artifact of Doppler imaging," filed on May 15, 2013, and (2) U.S. Provisional Patent App. No. 61/974,897, entitled "Method of detecting microbubbles in tissue and tissue phantoms using 'twinkling' artifact of Doppler imaging," filed on Apr. 3, 2014, the contents of which are fully incorporated by reference herein for all purposes.

STATEMENT OF U.S. GOVERNMENT INTEREST

This invention was made with government support under 2R01 EB007643-05, 1R01 CA154451, and 5K01EB015745-02, each awarded by the National Institutes of Health. The government has certain rights in the invention.

BACKGROUND

Unless otherwise indicated herein, the materials described in this section are not prior art to the claims in this application and are not admitted to be prior art by inclusion in this section.

As non-invasive therapy becomes increasingly favorable over invasive procedures, new challenges have risen in monitoring the progress of non-invasive therapies. Non-invasive therapies typically do not break the skin of the patient, thereby avoiding many of the risks associated with invasive treatments. For example, an invasive, surgical treatment may require a doctor or a machine to make incisions to a patient's skin and underlying tissue; non-invasive therapies, on the other hand, may be performed without having to make such incisions, thus allowing for a reduced recovery time and avoiding possible surgical errors.

Some non-invasive therapies may assist in the delivery and/or perfusion of a drug or gene to a certain tissue or at a desired location in a subject. Other non-invasive therapies may generate heat within a designated portion of the body. Although these non-invasive therapies avoid certain risks commonly associated with their invasive-therapy counterparts, they may potentially be harmful if incorrectly administered.

SUMMARY

Various embodiments set forth herein provide ways of detecting objects based on inducing a cavitation bubble in a medium. These embodiments are provided herein for purposes of illustration and are not meant to be limiting in any way.

In one aspect, a method is provided for imaging a cavitation bubble. The method may include producing a vibratory wave that induces a cavitation bubble in a medium. Further, the method may include producing one or more detection waves directed toward the induced cavitation bubble, where the one or more received reflection waves correspond to at least one of the one or more produced detection waves reflection from the induced cavitation bubble. Yet further, the method may include receiving one or more reflection waves, where the one or more received reflection waves correspond to at least one of the one or more produced detection waves reflecting from the induced cavitation bubble. In addition, the method may include identifying a change in one or more characteristics of the induced cavitation bubble, where the identified change in one or more characteristics corresponds to the one or more received reflection waves. In addition, based on the identified change in the one or more characteristics, the method may include generating an image of the induced cavitation bubble using a computing device on the basis of the identified change in the one or more characteristics.

In another aspect, a non-transitory computer-readable medium including program instructions that, when executed by a processor, cause the processor to perform functions. The functions may include producing a vibratory wave that induces a cavitation bubble in a medium. Further, the functions may include producing one or more detection waves directed toward the induced cavitation bubble, where the one or more received reflection waves correspond to at least one of the one or more produced detection waves reflection from the induced cavitation bubble. Yet further, the functions may include receiving one or more reflection waves, where the one or more received reflection waves correspond to at least one of the one or more produced detection waves reflecting from the induced cavitation bubble. In addition, the functions may include identifying a change in one or more characteristics of the induced cavitation bubble, where the identified change in one or more characteristics corresponds to the one or more received reflection waves. In addition, based on the identified change in the one or more characteristics, the functions may include generating an image of the induced cavitation bubble using a computing device on the basis of the identified change in the one or more characteristics.

In yet another aspect, a computing device may include a processor and a non-transitory computer-readable medium configured to store program instructions that, when executed by a processor, may cause the computing device to perform functions. The functions may include producing a vibratory wave that induces a cavitation bubble in a medium. Further, the functions may include producing one or more detection waves directed toward the induced cavitation bubble, where the one or more received reflection waves correspond to at least one of the one or more produced detection waves reflection from the induced cavitation bubble. Yet further, the functions may include receiving one or more reflection waves, where the one or more received reflection waves correspond to at least one of the one or more produced detection waves reflecting from the induced cavitation bubble. In addition, the functions may include identifying a change in one or more characteristics of the induced cavitation bubble, where the identified change in one or more characteristics corresponds to the one or more received reflection waves. In addition, based on the identified change in the one or more characteristics, the functions may include generating an image of the induced cavitation bubble using a computing device on the basis of the identified change in the one or more characteristics.

In yet a further aspect, an in vivo method for generating an image of a cavitation bubble may include administering a vibratory wave to a subject in need thereof to generate an image of a cavitation bubble in a medium within the subject. The method may include producing a vibratory wave that induces a cavitation bubble in a medium. Further, the method may include producing one or more detection waves directed toward the induced cavitation bubble, where the one or more received reflection waves correspond to at least one of the one or more produced detection waves reflection from the induced cavitation bubble. Yet further, the method may include receiving one or more reflection waves, where the one or more received reflection waves correspond to at least one of the one or more produced detection waves reflecting from the induced cavitation bubble. In addition, the method may include identifying a change in one or more characteristics of the induced cavitation bubble, where the identified change in one or more characteristics corresponds to the one or more received reflection waves. In addition, based on the identified change in the one or more characteristics, the method may include generating an image of the induced cavitation bubble using a computing device on the basis of the identified change in the one or more characteristics.

These as well as other aspects, advantages, and alternatives will become apparent to those of ordinary skill in the art by reading the following detailed description, with reference where appropriate to the accompanying drawings. Further, it should be understood that this summary and other descriptions and Figures provided herein are intended to illustrative embodiments by way of example only and, as such, that numerous variations are possible. For instance, structural elements and process steps can be rearranged, combined, distributed, eliminated, or otherwise changed, while remaining within the scope of the embodiments as claimed.

DETAILED DESCRIPTION

Figure 1:
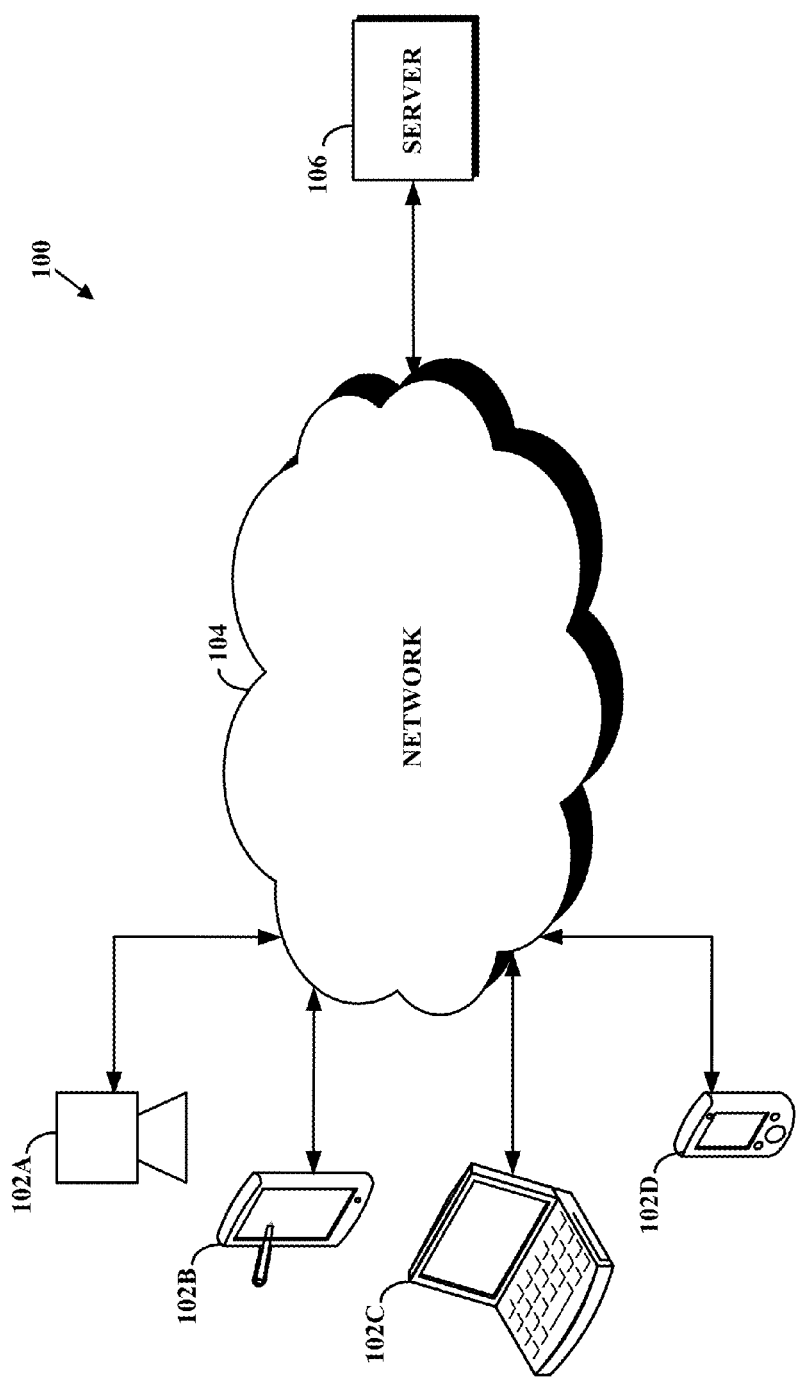
FIG. 1 shows a simplified block diagram of an example communication network in which at least one embodiment can be implemented.

In the following detailed description, reference is made to the accompanying Figures, which form a part thereof. In the Figures, similar symbols typically identify similar components, unless context dictates otherwise. The illustrative embodiments described in the detailed description, Figures, and claims are not meant to be limiting. Other embodiments may be utilized, and other changes may be made, without departing from the spirit or scope of the subject matter presented herein. It will be readily understood that aspects of the present disclosure, as generally described herein, and illustrated in the Figures, can be arranged, substituted, combined, separated, and/or designed in a wide variety of different configurations, all of which are explicitly contemplated herein.

1. OVERVIEW

Non-invasive therapies may involve introducing electromagnetic or acoustic energy into a subject. In one example, an ultrasound wave is introduced into a subject that induces cavitation bubbles at a desired location. Subsequent acoustic pulses may be administered that may interact with the induced cavitation bubbles, such that the changes in size and/or location of the induced cavitation bubbles may assist in the delivery and/or perfusion of the drug or gene. As non-invasive therapies become more prevalent, it may be desired to be able to accurately and sensitively monitor the progress of these therapies in real time. Note that a "subject" may herein refer to a human body, a body of a mammal, or any other body receiving a non-invasive therapy such as ultrasound therapy.

Passive cavitation detection (PCD) is one known method of detecting cavitation bubbles. A typical PCD configuration involves aligning a single-element hydrophone (or a similar sensor) to detect the reflection of acoustic waves from the cavitation bubbles. This reflection of acoustic waves from an object, such as a cavitation bubble, is often referred to as "backscatter." However, PCD does not provide spatial information about the induced bubbles. As a result, PCD is an ineffective method of monitoring the progress of ultrasound therapies.

B-mode imaging is another known method of detecting objects within a medium. B-mode imaging utilizes an array of transducers to transmit acoustic pulses and measure acoustic pulses reflecting from an object within a medium. While B-mode imaging provides spatial information that may be used in the generation of a two-dimensional image, it is only sensitive to objects larger than induced cavitation bubbles. Thus, B-mode imaging is also an ineffective method of monitoring the progress of ultrasound therapies.

Other known methods of improving ultrasound involve introducing particles into a subject's body, such as ultrasound contrast agents (UCAs). One example UCA is a magnetic resonance imaging (MRI) contrast agent that can be detected using an MRI scanner or the like. However, magnetic contrast agents are expensive and not widely available. Other UCAs include artificial microbubbles—microbubbles that have been created outside of a subject's body—that may be introduced into a subject intravenously. While these artificial microbubbles may increase the sensitivity or contrast of an ultrasound imaging method, the artificial microbubbles are prone to collapse prior to arriving at the desired tissue or location and often collapse while interacting with ultrasound waves. Accordingly, artificial microbubbles may need to be regularly administered, and the resulting imaging may be inconsistent or unreliable.

In an example embodiment, a computing device may produce one or more waves for imaging cavitation bubbles in a medium. In some instances, the computing device may produce a vibratory wave from a probe coupled to the computing device to induce the cavitation bubbles in the medium. The computing device may also produce detection waves having known characteristics from a probe directed toward the cavitation bubbles. Some of the detection waves may reflect from the cavitation bubbles, thereby producing reflection waves whose characteristics may differ from those of the detection waves. Some examples of wave characteristics include amplitude, frequency, and phase. Some of the reflection waves may return to the computing device and/or probe, or possibly another device, probe, or sensor connected to the computing device. The computing device may then process the received reflection waves in order to identify a change in the characteristics of the cavitation bubbles. The identified change in the characteristics may then be used as a basis to generate an image of the cavitation bubbles.

In some instances, a frequency of the detection waves may be different from a frequency of the reflection waves. This frequency change may be detected and used as a basis to generate an image of the cavitation bubbles. This frequency change may be herein referred to as the Doppler effect. As one example, a detection wave may reflect from a transient cavitation bubble, where the size of the bubble may be changing or shrinking. In this example, a wave reflecting from the shrinking cavitation bubble may experience a shift in frequency as a result of the bubble size shrinking. The computing device may process shift in frequency (from the frequency of the detection wave to the frequency of the reflection wave) and generate a visual representation of that frequency shift. In one embodiment, displaying the visual representation of that frequency shift may include selecting a color based on the difference in frequencies and displaying that color on a graphical display.

In some instances, the vibratory wave may also interact with cavitation bubbles that had been previously produced from a different vibratory wave, excitation source, depressurization, and/or any other event that induces cavitation bubbles. In this instance, the vibratory wave may, in addition to inducing new cavitation bubbles, interact with the previously produced cavitation bubbles. The interaction may change a variety of characteristics of the previously produced cavitation bubbles, such as the size, shape, position, velocity, and/or the overall distribution of the previously produced cavitation bubbles. In one example, the vibratory wave may be repeated periodically in order to induce new cavitation bubbles, as well as interact with previously produced cavitation bubbles, thereby causing a change to the overall distribution of the cavitation bubbles.

In some instances, the detection waves may reflect from the induced cavitation bubbles, without inducing new cavitation bubbles. In this instance, the detection waves may interact with the cavitation bubbles already induced (herein also referred to as "induced cavitation bubbles"). In some instances, the detection waves may interact with induced cavitation bubbles in addition to reflecting from the induced cavitation bubbles. Thus, the characteristics of the cavitation bubbles may be changed. Yet, in this instance, the detection waves may not, for example, have a sufficient amplitude to induce new cavitation bubbles. Note that the detection waves may have a smaller amplitude compared to the vibratory wave. Thus, the induced cavitation bubbles resulting from the detection waves are less significant than the induced cavitation bubbles resulting from interaction with the vibratory wave.

In one example, the detection waves may all have nearly identical wave characteristics. In this example, the measuring the reflection waves caused by nearly identical detection waves reflecting from the cavitation bubbles over a period of time may provide information about the cavitation bubble's transient behavior. For instance, if the detection waves do not significantly alter the characteristics of the cavitation bubbles when reflecting from them, then producing nearly identical detection waves over time may produce reflection waves indicative of the naturally-changing characteristics of the cavitation bubbles.

In one instance, the induced cavitation bubbles are micrometer-sized or submicron-sized. An induced cavitation bubble may combine with another cavitation bubble to form a larger bubble. Additionally, the cavitation bubbles may be transient, such that they may shrink over time and eventually collapse. If an object is present within the medium, the cavitation bubbles may form in close proximity with the object. In one example, the bubbles form near cracks and/or crevices of the object, and may become trapped within those cracks and/or crevices.

In one instance, the timing of the produced vibratory waves, detection waves, and periods of inactivity in between those waves may be varied. Any length of time in which the transducer is not producing a wave may be referred to herein as a "period of inactivity." In one example, there is a period of inactivity between the vibratory wave and the detection waves. In another example, the duration of the vibratory waves and the detection waves may be increased or decreased in order to produce desired results for a variety of scenarios. As one example, one medium may require a longer duration of the vibratory wave in order to induce the desired cavitation bubbles compared to a different medium.

In one example, the generated image representing a change in the characteristics of the cavitation bubbles may be produced in real time or near-real time. In this example, the image may be displayed on a graphical display that is connected or coupled to the computing device. This image may require a number of pixels in order to display at a variety of resolutions, depending on a variety of factors such as transducer sensitivity, the number of transducers used to produce the waves, the number of sensors used to detect the change in characteristics of the cavitation bubbles, and/or a desired resolution based on instructions stored on the computing device, among other possibilities. In another example, the generated image representing a change in the characteristics of the cavitation bubbles is produced at a time that is significantly later than the time the reflection waves were received. In this example, data representing the reflection waves, along with data representing the detection waves, may be stored onto a storage device for later processing. The later-processed data representing the reflection waves may be produced as a compressed image or a vector image, either of which may then be printed, stored, displayed, or otherwise made available for observation.

2. EXAMPLE ARCHITECTURE

FIG. 1 shows a simplified block diagram of an example communication network in which at least one embodiment can be implemented. It should be understood that this and other arrangements described herein are set forth only as examples. Those skilled in the art will appreciate that other arrangements and elements (e.g., medical devices, laboratory machines, interfaces, functions, orders, and groupings of functions, etc.) can be used instead and that some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. And various functions described herein may be carried out by a processor executing instructions stored in memory.

As shown in FIG. 1, example network 100 includes various network-access devices 102A-102D, network 104 such as the Internet, and server 106. As illustrated, network-access devices 102A, 102B, 102C, and 102D may be a computing device (e.g., a portable medical device), a tablet computer, a laptop computer and/or a desktop personal computer (PC), and a mobile phone, respectively. It should be noted that network-access device 102A may be described as a computing device for carrying out process, methods, and functions further described herein. As such, network-access devices 102B-102D, network 104, and server 106 may be described for purposes of illustrating that various processes, steps, and/or functions may be distributed and performed by other devices, networks, and/or servers. For example, network-access devices 102B-102D may be standalone devices or may be coupled to network-access device 102A for carrying out various processes. Thus, it should be noted that additional entities and devices not depicted in FIG. 1 could be present as well.

Network 104 may be a public network or a private network (e.g., a local network in a laboratory, a clinic, and/or a doctor's office). As an example, there could be more network-access devices and more servers in communication with network 104. Other network elements may be in communication with network 104 as well. Also, there could be one or more devices and/or networks making up at least part of one or more of the communication links depicted in FIG. 1. As an example, there could be one or more routers, switches, or other devices or networks on the communication links between network-access devices 102A-102D, network 104, and/or server 106. Each of network-access devices 102A-102D may be any network-access device arranged to carry out the network-access device functions described herein.

Systems and devices in which example embodiments can be implemented will now be described in greater detail. In general, an example system may be implemented in and/or can take the form of a computing device. In an example embodiment, network-access device 102A may be described as a computing device including an engine capable of producing detection waves and receiving reflection waves. Further, the computing device may be portable, hand-held, and/or transferrable by a single person.

Figure 2:
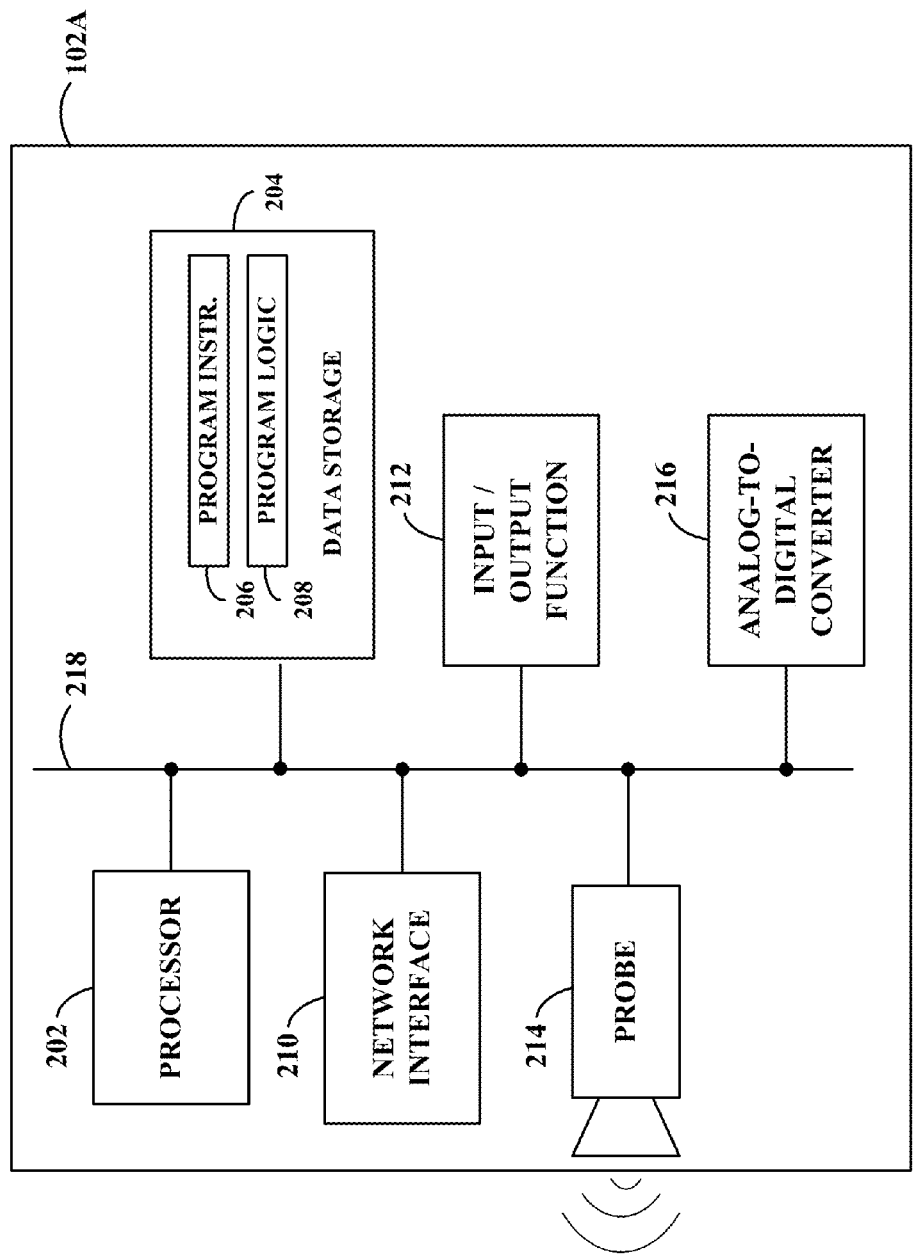
FIG. 2 shows a simplified block diagram of a network-access device arranged to implement aspects of at least one embodiment.

FIG. 2 shows a simplified block diagram of a computing device arranged to implement aspects of at least one embodiment. For example, network-access device 102A may include processor 202, data storage 204, and network interface 210, all linked together via system bus, network, or other connection mechanism 218.

Processor 202 may include one or more general purpose microprocessors, central processing units (CPUs), and/or dedicated signal processors. In addition, processor 202 may include one or more application specific integrated circuits (ASICs), digital signal processors (DSPs), and may be integrated in whole or in part with network interface 210. Data storage 204 may include memory and/or other storage components, such as optical, magnetic, organic or other memory disc storage, which can be volatile and/or non-volatile, internal and/or external, and integrated in whole or in part with processor 202. Data storage 204 may be arranged to contain (i) program instructions 206 and (ii) program logic 208, executable by processor 202. Data storage 204 may also store data that may be manipulated by processor 202 to carry out the various methods, processes, or functions described herein.

In some embodiments, these methods, processes, or functions can be defined by hardware, firmware, and/or any combination of hardware, firmware and software. Therefore, data storage 204 may include a tangible, non-transitory computer-readable medium, having stored thereon program instructions that, upon execution by one or more processors, cause computing device 102A to carry out any of the methods, processes, or functions disclosed in this specification or the accompanying drawings.

Although these components are described herein as separate data storage elements, the elements could just as well be physically integrated together or distributed in various other ways. For example, program instructions 206 may be maintained in data storage 204 separate from program logic 208, for easy updating and reference by program logic 208.

Network interface 210 may enable network-access device 102A to send communication and receive communication. Network interface 210 typically functions to communicatively couple network-access device 102A to networks, such as network 104. As such, network interface 210 may include a wired (e.g., Ethernet) and/or wireless (e.g., Wi-Fi, BLUETOOTH®, or a wide-area wireless connection) packet-data interface, for communicating with other devices, entities, and/or networks.

Input/output function 212 may facilitate user interaction with an example computing device 100. Input/output function 212 may comprise multiple types of input devices, such as a keyboard, a mouse, a touch screen, a probe, a transducer, a sensor, and/or any other device that is capable of receiving input. Similarly, input/output function 212 may comprise multiple types of output devices, such as a graphical display, a printer, one or more light emitting diodes (LEDs), speaker configured to generate audible sounds, or any other device that is capable of providing output discernible to a user. Additionally or alternatively, example computing device 102E may support remote access from another device, via network interface 210 or via another interface (not shown), such an RS-132 or Universal Serial Bus (USB) port.

Probe 214 may produce one or more detection waves that may include radio frequency pulses, a sound wave, a sound pressure wave, and/or an oscillating sound pressure wave. In particular, probe 214 may produce such pulses in response to executing program instructions 206 stored in data storage 204 and communicating to probe 214 via other connection mechanism 218. Probe 214 may also produce waves within one or more time periods. Yet further, in some instances, any one of the waves may be produced within a given time period and other detection waves may be produced within a different time period. In some instances, probe 214 may produce, ultrasound propagation or arrays, Doppler waves, among other possibilities. In particular, probe 214 may produce one or more pulses that contain a series of 4-30 pulses or bursts, 1-10 cycles of such bursts, and where the pulses are transmitted with a frequency of 1 to 40 MHz. In some instances, the pulses may have a 1 Hz to 20 kHz pulse-repetition frequency (PRF). It should be noted that a probe, such as probe 214, may be similar to a transducer such that a probe and a transducer may be used interchangeably herein.

In some instances, probe 214 may produce one or more vibratory waves, such as high-intensity focused ultrasound (HIFU) waves. The one or more vibratory waves may be configured to induce cavitation bubbles within a medium. The one or more vibratory waves may also include radio frequency pulses, radio frequency pulses produced within a first time period (e.g., 100 microseconds), a sequence of substantially similar radio frequency pulses produced within a time period different than the first time period, a sound wave, a sound pressure wave, and/or an oscillating sound pressure wave. In the examples above, the first time period may be 10 microseconds to 100 milliseconds, among other possible ranges. Further, in some instances, vibratory waves may be transmitted at a frequency of approximately 100 kHz to 10 MHz and have a 1 Hz to 20 kHz PRF. Yet further, in some instances, positive pressures (P+) and negative pressures (P−) of pressure detections waves may be 2 to 150 MPa and −150 to −2 MPa, respectively. Probe 214 may also receive waves reflected from external objects back to probe 214. Computing device 100 may also receive waves through a sensor or another device, possibly connected through input/output function 212. As noted, vibratory waves may be configured to induce cavitation bubbles in a medium. As such, it should be understood that the above-characteristics of vibratory waves may be configured to induce cavitation bubbles in a medium.

It should be noted that probe 214 may be removable so as to operate while being physically separate from computing device 100. For example, probe 214 may communicate remotely with computing device 110 through input/output function 212. In some instances, there may be several probes similar to probe 214 that may move remotely, controlled by computing device 110.

It should also be noted that probe 214 may include more than one transducer, and that the transducers may be arranged to form an array. Each transducer may then be independently controlled to emit one or more vibratory waves or one or more detection waves as previously described. Computing device 102A may include programs that control each of the transducers of probe 214, such that phases of waves emitted from each transducer may be adjusted in order to electronically change the direction that the resulting wave is emitted. In other words, by controlling the timing in which each transducer emits a detection wave, a specific direction may be selected in which the emitted detection waves constructively interfere to form a directional acoustic beam. An electronically controlled array of transducers capable of changing the direction of a constructed beam may be herein referred to as a "phased array."

Reflected waves received by probe 214 may be converted to digital waves through analog-to-digital converter (ADC) 216. ADC 216 may be a 12-24 bit analog-to-digital converter configured to sample waves at a 10-30 MHz frequency. For example, waves transmitted by probe 214 may be received by probe 214 and converted to digital waves through ADC 216. In some instances, digitized waves from ADC 216 may also be processed in real-time using mathematical software platforms. In some instances, unmodified wave outputs from ADC 216 may identify characteristics of objects for detecting the objects. It should be noted that computing device 102A may also include one or more digital-to-analog converters (not illustrated) that may be configured to transmit waves to probe 214. As such, probe 214 may produce detection waves as described herein.

In some instances, computing device 102A may modify the reflected waves received by probe 214. In some instances, waves indicative of reflective waves may be modified by band-pass filters, analog filters, amplifiers, and clipping diodes (not shown in FIG. 2). In particular, waves may be modified by an anti-aliasing band-pass filter with a 0.7 to 17 MHz bandwidth. Further, waves may be amplified using time-gain compensation. Yet further, waves may be limited and/or clipped by a diode. In some instances, the modification described herein may be implemented through signal processing software. It should be noted that the above-referenced modifications to the reflected waves may occur before being sampled by ADC 216.

Figure 3:
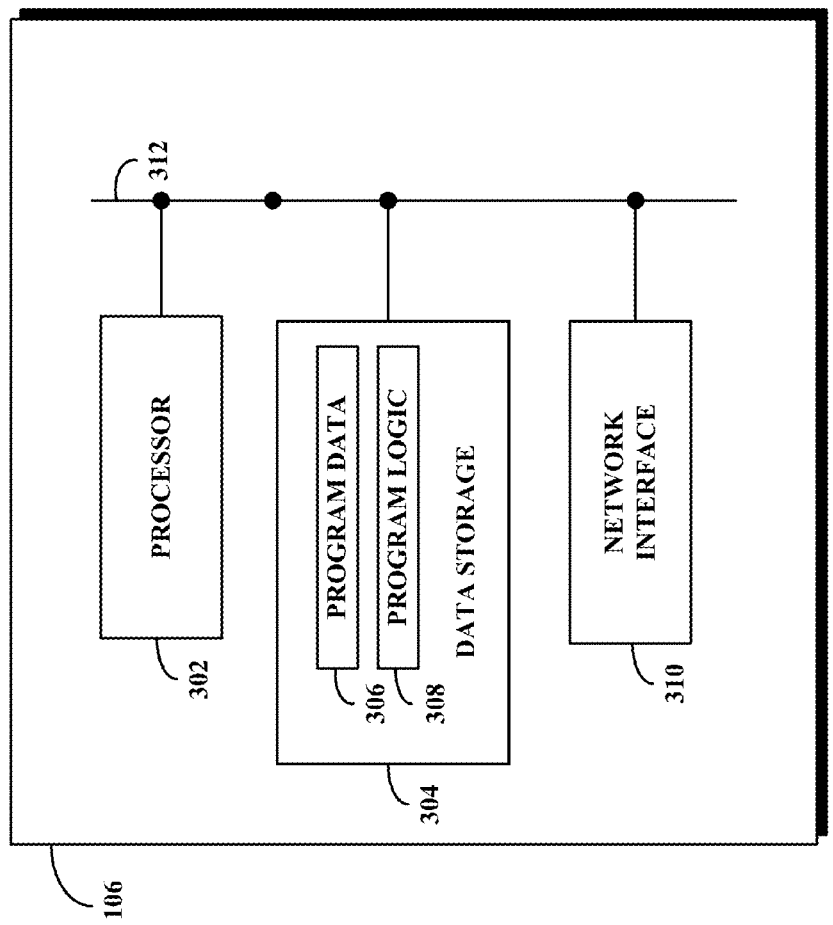
FIG. 3 shows a simplified block diagram of a server arranged to implement aspects of at least one embodiment.

Server 106 may be any network server or other computing system arranged to carry out the server functions described herein including, but not limited to, those functions described with respect to FIGS. 5-10. In particular, reflection wave received by probe 214 may be communicated to server 106 for analysis, possibly to detect an excited object. As such, network-access device 102A and server 106 may share processes, methods, and/or functions described herein for determining the presence of the excited object. FIG. 3 shows a simplified block diagram of a server arranged to implement aspects of at least one embodiment. As such, as shown in FIG. 3, server 106 may include processor 302, data storage 304 including program data 306 and program logic 308, and network interface 310, all linked together via system bus, network, and/or other connection mechanism 312. Processor 302, data storage 304, program data 306, program logic 308, and network interface 310 may be configured and/or arranged similar to processor 202, data storage 204, program instructions 206, program logic 208, and network interface 210, respectively, as described above with respect to network-access device 102A.

Data storage 304 may contain information used by server 106 in operation. For example, date storage 304 may include instructions executable by the processor for carrying out the server functions described herein including, but not limited to, those functions described below with respect to FIGS. 5 through 10. As another example, data storage 304 may contain various design logic and/or design data used for determining a test result, such as the logic and data described below with respect to FIGS. 5 through 10. Generally, data storage 304 may contain information used by server 106 to provide information accessible by various network-access devices, such as network-access device 102A, over network 104.

Returning to FIG. 1, network 104 may also include one or more wide area networks, one or more local area networks, one or more public networks such as the Internet, one or more private networks, wired networks, wireless networks, and/or networks of any other variety. Devices in communication with network 104 (including, but not limited to, network-access devices 102A-102D and server 106) may exchange data using a packet-switched protocol such as IP, and may be identified by an address such as an IP address.

Figure 4:
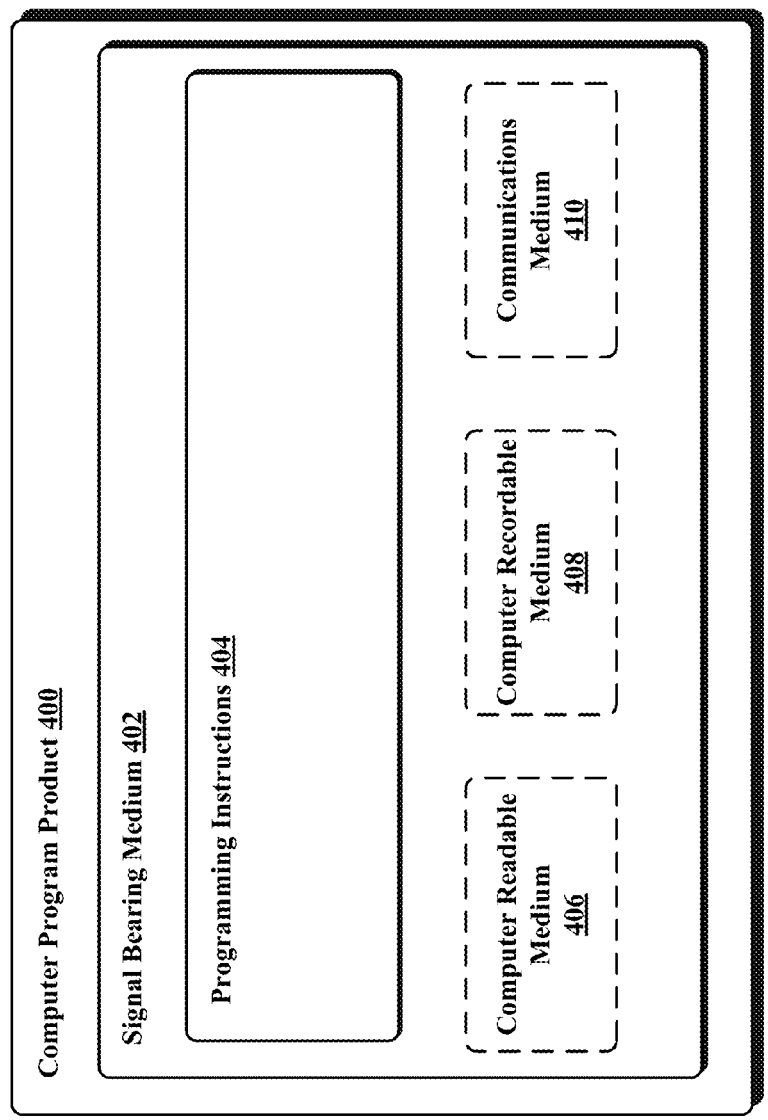
FIG. 4 depicts an example computer-readable medium arranged to implement aspects of at least one embodiment.

As noted above, in some embodiments, the disclosed methods may be implemented by computer program instructions encoded on a physical and/or non-transitory computer-readable storage media in a machine-readable format, or on other non-transitory media or articles of manufacture. FIG. 4 is a schematic illustrating a conceptual partial view of an example computer program product that includes a computer program for executing a computer process on a network-access device, arranged according to at least some embodiments presented herein.

In one embodiment, the example computer program product 400 is provided using a wave bearing medium 402. The wave bearing medium 402 may include one or more programming instructions 404 that, when executed by one or more processors may provide functionality or portions of the functionality described herein. In some examples, the wave bearing medium 402 may encompass a computer-readable medium 406, such as, but not limited to, a hard disk drive, a Compact Disc (CD), a Digital Video Disk (DVD), a digital tape, memory, etc. In some implementations, the wave bearing medium 402 may encompass a computer recordable medium 408, such as, but not limited to, memory, read/write (R/W) CDs, R/W DVDs, etc.

In some implementations, the wave bearing medium 402 may encompass a communications medium 410, such as, but not limited to, a digital and/or an analog communication medium (e.g., a fiber optic cable, a waveguide, a wired communications link, a wireless communication link, etc.). Thus, for example, the wave bearing medium 402 may be conveyed by a wireless form of the communications medium 410. It should be understood, however, that computer-readable medium 406, computer recordable medium 408, and communications medium 410 as contemplated herein are distinct mediums and that, in any event, computer-readable medium 408 is a physical, non-transitory, computer-readable medium.

The one or more programming instructions 404 may be, for example, computer executable and/or logic implemented instructions. In some examples, a computing device such as the network-access device 102A of FIG. 2 may be configured to provide various operations, functions, or actions in response to the programming instructions 404 conveyed to the network-access device 102A by one or more of the computer readable medium 406, the computer recordable medium 408, and/or the communications medium 410.

The physical and/or non-transitory computer readable medium could also be distributed among multiple data storage elements, which could be remotely located from each other. The computing device that executes some or all of the stored instructions could be a network-access device such as the network-access device 102A illustrated in FIG. 2. Alternatively, the computing device that executes some or all of the stored instructions could be another computing device, such as a server, for instance server 106 illustrated in FIG. 3.

3. EXAMPLE METHOD FOR IMAGING A CAVITATION BUBBLE

Figure 5:
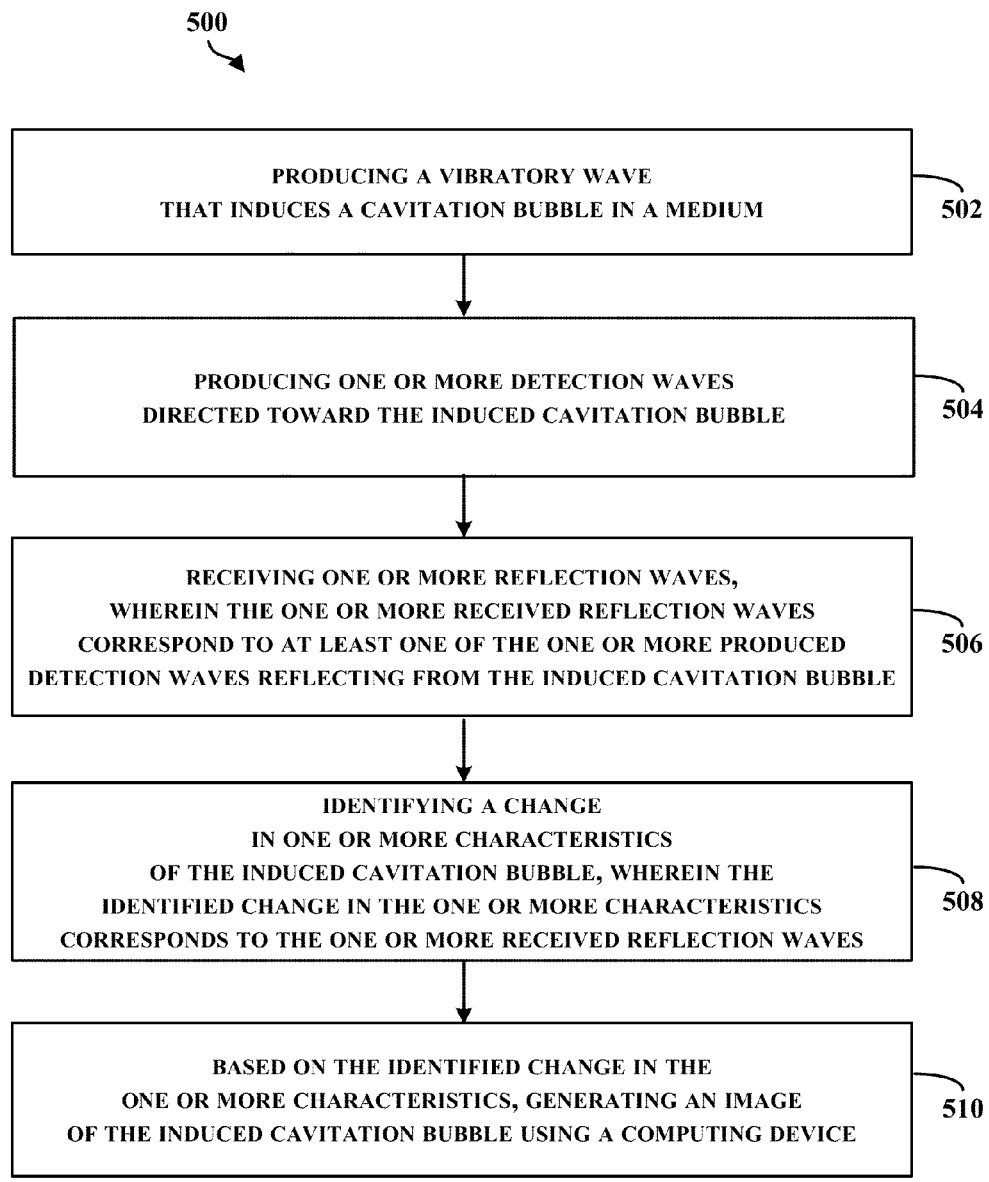
FIG. 5 is a simplified flow chart depicting aspects of an example method.

FIG. 5 shows a simplified flow chart depicting aspects of an example method for imaging a cavitation bubble as described herein. For purposes of example and explanation, aspects of such example methods are described with reference to an example computing device. It should be understood, however, that the example methods described herein may apply just as well to any suitable computing device including, but not limited to, a computing device integrated with a computer, a mobile computing device, a medical device, and/or other computing system, among other examples.

Figure 6A:
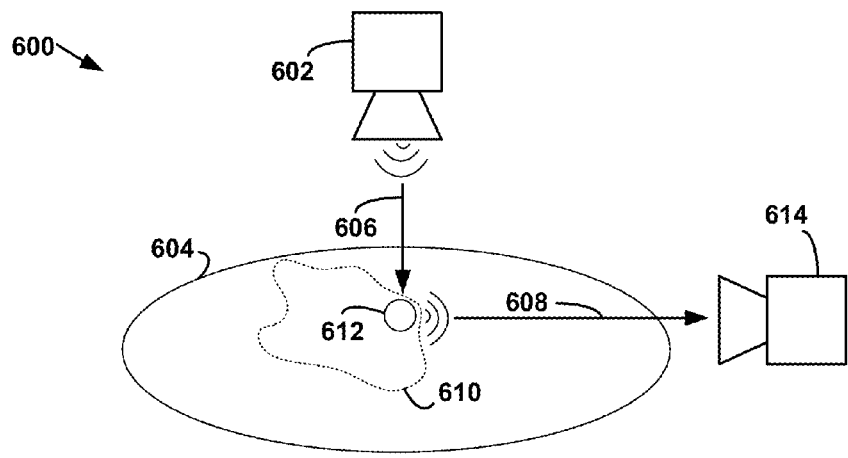
FIG. 6A depicts aspects of a computing device in accordance with one or more example embodiments.
Figure 6B:
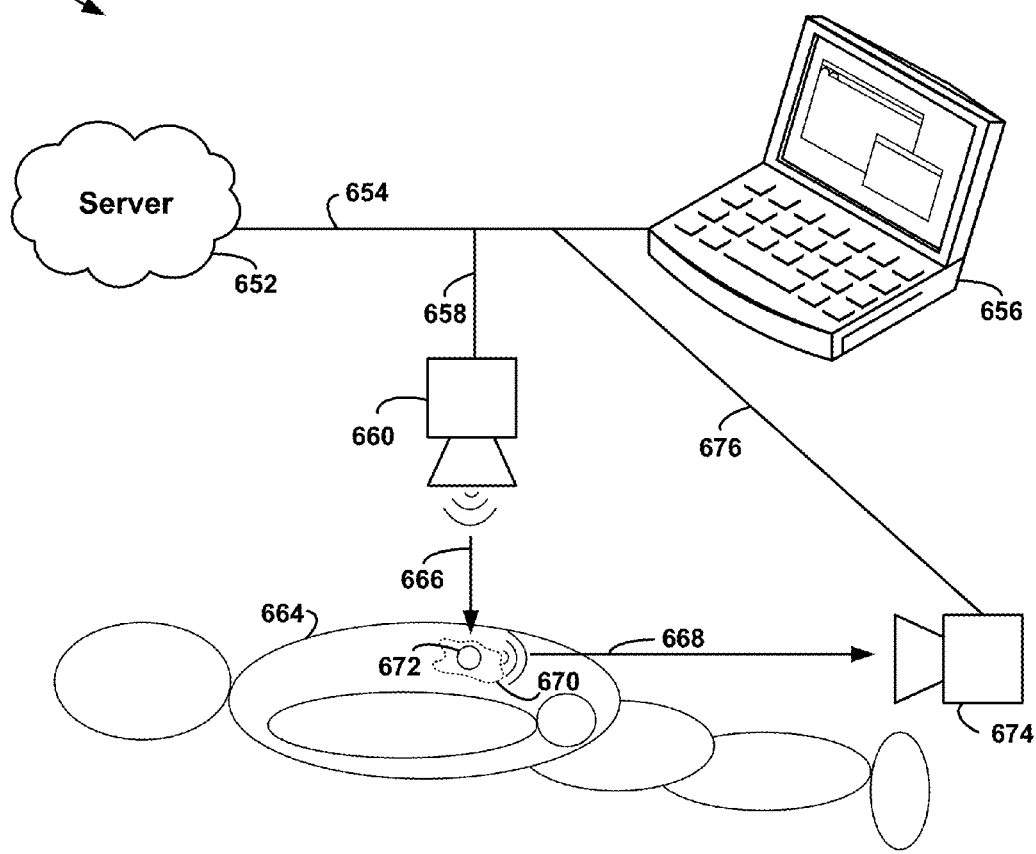
FIG. 6B depicts aspects of another computing device in accordance with one or more example embodiments.

FIGS. 6A and 6B depict aspects of example computing devices in accordance with one or more example embodiments. More particularly, FIGS. 6A and 6B depict aspects of a computing device illustrated in FIG. 5 for carrying out the method for imaging the cavitation bubble. For example, computing device 602 depicts aspects of an example computing device imaging a cavitation bubble. Various respective features, characteristics, and/or functionality of the computing devices depicted in FIGS. 6A and 6B are discussed further below with respect to the example methods described herein.

In FIG. 5, method 500 is described by way of example as being carried out by a computing device, possibly a computing device coupled to one or more probes. For example, method 500 may be carried by network-access device 102 and/or computing device 602. Further, example methods, such as method 500, can be carried out by devices other than a computing device and/or can be carried out by sub-systems in a computing device. For example, method 500 may also be carried out by network-access devices 102B-102D, network 104, and/or server 106. In some instances, an example method can be carried out by a computing device which is programmed to display a representation of cavitation bubbles on a graphical display.

As shown in FIG. 5, method 500 begins at block 502 with a computing device, such a computing device coupled to a probe, which may carry out functions for producing a vibratory wave that induces a cavitation bubble in a medium. At block 504, the computing device produces one or more detection waves directed toward the induced cavitation bubble. At block 506, the computing device receives one or more reflection waves, wherein the one or more received reflection waves corresponds to at least one of the one or more produced detection waves reflecting from the induced cavitation bubble. At block 508, the computing device identifies a change in one or more characteristics of the induced cavitation bubble, wherein the identified change in the one or more characteristics corresponds to the one or more received reflection waves. At block 510, based on the identified change in the one or more characteristics, the computing device generates an image of the induced cavitation bubble.

The steps of method 500 are explained in the following subsections. Although method 500 may be carried out by network-access device 102A, this is not required. Various steps illustrated by these flow charts may be carried out by other types of devices or systems, such as server 106. Further, it may be possible to distribute aspects of individual steps between network-access devices 102A-102B, network 104, and server 106. For instance, network-access device 102A may produce detection waves and receive reflection waves and server 106 may determine the presence of the object in the excited state.

As noted, FIGS. 6A and 6B depict aspects of example computing devices in accordance with one or more example embodiments. FIG. 6A depicts aspects of a computing device in accordance with one or more example embodiments. In FIG. 6A, scenario 600 provides a computing device 602 that may be positioned adjacent to medium 604. In some instances, computing device 602 may be similar as computing device 102A in FIGS. 1 and 2. Yet, further, computing device 602 may be configured to communicate with other computing devices, such as another computing device described in further detail in FIG. 6B. Additionally, computing device 614 may be positioned confocally with computing device 602. Further, computing device 614 may also be configured to communicate with other computing devices, such as another computing device described in further detail in FIG. 6B.

In some embodiments, medium 604 may be part of a human body or an organ encompassing object 610. Medium 604 may be bodily tissue, cancer tissue, or a variety of other bodily fluids, among other examples. Object 610 may be a variety of solid objects inside the body (e.g., a bullet from a handgun, a catheter, or a stent), including calcifications and foreign objects introduced from outside of the body, among other examples. Note that object 610 is not required for the method used to image a cavitation bubble in a medium, but is optional and may or may not be present in the body, as indicated by the dotted line as shown in FIG. 6A and FIG. 6B. Other examples of mediums and objects may exist.

In some embodiments, object 610 may include reflection items that may be used to help detect the presence of object 610 in medium 604. In some instances, reflection items may include a bubble, a calcification, a crevice, a crack, and/or a concretion associated with the object. For example, a reflection item may be bubble 612 on object 610. In some instances, bubble 612 may be in a crack and/or crevice of object 610. As a general matter, it should be noted that bubbles may also be formed in free fluid, concretions, and/or tissues in a mammal. For example, bubble 610 may be formed on any of the example objects described above for object 610. Further, in some instances, a bubble, such as bubble 612, may include trapped air, a gas pocket, and/or air emboli. In addition, bubble 612 may be stationary or in motion while on the surface of object 610.

FIG. 6B depicts aspects of another computing device in accordance with one or more example embodiments. In FIG. 6B, scenario 650 provides a computing device 660 that may be positioned adjacent to medium 664. In some instances, computing device 660 may be similar to computing device 102A and/or computing device 602. In FIG. 6B, medium 664 may be a fluid or tissue within a human body or the body of some other living mammal. As a general matter, object 670 may be similar to object 610 and bubble 672 may be similar to bubble 612. The medium 664 and object 670 may be similar to medium 604 and object 610, respectively.

a. Producing a Vibratory Wave

As noted for block 502 of FIG. 5, a computing device may carry out functions for producing a vibratory wave that induces a cavitation bubble in a medium. As illustrated in FIG. 6A, computing device 602 may produce a vibratory wave. For example, computing device 602 may produce pulses in a direction 606 toward medium 604 and, if present, object 610. In some instances, computing device 602 may produce pulses that penetrate the surface of medium 604 and induce cavitation bubble 612 therein. Further, computing device 602 may change characteristics of the vibratory wave so as to induce fewer or more cavitation bubbles of various sizes. Yet further, computing device 602 may change characteristics of the vibratory wave so as to interact with the cavitation bubble 612, such that the cavitation bubble may increase in size, change its position, and/or oscillate in its current position.

In some embodiments, computing device 602 may produce vibratory waves that are focused on a region within the medium 604. In some instances, computing device 602 may produce vibratory waves focused on a region in close proximity to bubble 612. The focusing of the vibratory wave may be done mechanically using, for example, a curved transducer, or electronically using, for example, a phased array, as previously described. In some instances, the computing device 602 may change the direction of focus so as to produce vibratory waves to induce new cavitation bubbles at a new location. As one example, the focus may sweep across a specified area over time to as to induce cavitation bubbles at a variety of positions. Other possibilities may also exist.

In some embodiments, the bubble 612 forms in close proximity to object 610. Note that object 610 may or may not exist within medium 604; this is denoted by the dotted line of object 610. Some examples of object 610 include, but are not limited to: a urinary tract stone, a kidney stone, a ureter stone, a bladder stone, a urethra stone, a prostate stone or a prostatic stone, a salivary stone, a gallbladder stone, a gall stone, a bile duct, a stone in the bile duct, a blood clot, stool, cerumen, a calcification, a calcified plaque, an atherosclerotic plaque, a struvite, calcium oxalate monohydrate (COM), a cystine, a tonsil stone, an artificial object, and an object introduced inside the subject's body, among other objects.

In some embodiments, the bubble 612 forms within a medium in which object 610 is absent. As an example, a therapy may be performed on bodily tissue of a subject, such that no object is present within the bodily tissue or is related to the therapy. Some examples of medium 604 include, but are not limited to: bodily tissue, cancer tissue, water, blood, urine, bile, mucus, pus, semen, saliva, pericardial fluid, peritoneal fluid, pleural fluid, gastric fluid, stool, synovial fluid, cerebrospinal fluid, lymph, and exudate, among other mediums.

In some embodiments, computing devices 602 and 660 may produce different vibratory waves. The vibratory wave emitted may include any one of the following: radio-frequency pulses, microwave pulses, optical pulses, and acoustic pulses, among other pulses.

In some embodiments, various modes may be employed by computing devices 602 and 660 to produce the vibratory waves. For example, the vibratory waves may vary in length, and they may be pulsed periodically in order to induce new cavitation bubbles and/or interact with existing cavitation bubbles. In some instances, such pulses may be produced with a 3 kHz pulse-repetition frequency (PRF). Further, the PRF may be adjusted and/or modified according to the dimensions of object 610 and/or bubble 612. Yet further, characteristics of the vibratory waves may change between each pulse to provide desired results. As one example, a first vibratory wave might have a larger amplitude compared to subsequent vibratory waves, such that the subsequent vibratory waves interact with and/or grow the previously induced cavitation bubbles. In this example, the PRF may be configured to emit vibratory waves so most of that the initially induced cavitation bubbles do not collapse and are maintained with each periodic pulse of the vibratory waves.

In some instances, the direction of the vibratory wave may be changed over time so as to induce cavitation bubbles over a larger area. In this instance, the direction in which the vibratory waves are emitted may change in between pulses, or while the pulse is being emitted. The direction may be changed mechanically and/or electronically.

b. Producing One or More Detection Waves

As noted for block 504 of FIG. 5, a computing device may carry out functions for producing one or more detection waves directed toward the induced cavitation bubble. As illustrated in FIG. 6A, computing device 602 may also produce detection waves. For example, computing device 602 may produce detection waves in a direction 606 toward medium 604 and, if present, object 610. In some instances, computing device 602 may produce pulses that penetrate the surface of medium 604 and reflect from cavitation bubble 612 therein. Further, computing device 602 may change characteristics of the detection waves depending on the characteristics of the medium 604 and the cavitation bubble 612. Yet further, computing device 602 may change characteristics of the detection waves so as to interact with the cavitation bubble 612, such that the cavitation bubble may increase in size, change its position, and/or oscillate in its current position.

In some embodiments, computing device 602 may produce detection waves that are focused on a region of object. In some instances, detection waves may be focused on a reflection item. For example, computing device 602 may produce detection waves focused or directed to bubble 612. For instance, referring back to FIG. 2, detection waves may be focused or directed toward a given bubble by positioning probe 214 in a given manner. In some instances, probe 214 may be angled in such a way to direct detection waves towards the given bubble. As such, the detection waves may be focused on the left side of bubble 612. In some instances, detection waves may be directed towards the left side of bubble 612 and then the waves may be directed towards to the right side of bubble 612. Other possibilities may also exist.

In some embodiments, computing devices 602 and 660 may produce different types of detection waves. In some instances, the detection waves may be Doppler waves with multiple pulses. Further, detection waves may be a B-mode with plane waves. Yet further, detection waves may include a pulse sequence with peak positive pressures (P+) and peak negative pressures (P−).

As a general matter, detection waves may include one or more bursts such that each burst includes a number of pulses. For example, a single pulse sequence may include 14 pulses. It should be noted that each detection wave may also have one or more of cycles such that each cycle includes a burst and a time period before or after the burst. It should be noted that detection waves may include a range of 2 to 20 bursts. Yet further, detection waves may include 1 to 7 cycles of bursts and time periods without bursts.

In some embodiments, a variation of the different waves may be produced. For example, detection waves may be produced to interact with bubble 612 or 672, possibly driving bubble 612 or 672 into oscillation. In addition, detection waves may be produced and reflection waves may be received that reflected from bubble 612 or 672. In particular, the reflection waves may include phase variations or phase variability indicative of the cavitation bubble 612. Thus, the reflection waves may be processed to identify characteristics of the cavitation bubble 612 or 672, and those characteristics may be used to generate an image of the cavitation bubble 612 or 672. Other possibilities may also exist.

In some embodiments, detection waves may be produced and directed to a human body. For example, referring back to FIG. 6B, computing device 660 may produce detection waves in a direction 666 toward medium 664 and bubble 672. In some instances, computing device 660 may produce pulses that penetrate the surface of medium 664 to reflect off of bubble 672, possibly returning in a direction 668 toward computing device 674. In other embodiments, the reflection waves may return back to computing device 660.

c. Receiving One or More Reflection Waves

As noted for block 506 of FIG. 5, a computing device may carry out functions for receiving one or more reflection waves, wherein the one or more received reflection waves correspond to at least one of the one or more produced detection waves reflecting from the induced cavitation bubble. As noted for FIG. 6A, computing device 602 may produce detection waves in a direction 606 toward medium 604 and bubble 612. The reflected waves may return in a direction 608 toward computing device 614 so as to be received by computing device 614. In some instances, computing device 614 may be aligned confocally with computing device 602. In other embodiments, the reflection waves return to computing device 602 in a direction opposite of direction 606. In some instances, computing devices 602 and 614 may be placed 5-15 centimeters away from medium 604 when sending and receiving pulses and in other instances, computing devices 602 and 614 may be farther away from, or closer to, medium 604. In other instances, computing devices 602 and 614 may make contact with the outer surface of medium 604 when sending and receiving pulses.

In a similar manner, FIG. 6B illustrates reflected waves reflecting in a direction 668 toward computing device 674. Further, reflection waves may indicate the presence of bubble 672, and the characteristics of the reflection waves may possibly indicate one or more characteristics of the bubble 672. It should be noted that one or more pressure waveforms produced by computing device 660 may be measured by a hydrophone associated with computing device 660, possibly integrated within computing device 660 and/or 674.

d. Identifying a Change in One or More Characteristics of the Induced Cavitation Bubble As noted for block 508 of FIG. 5, a computing device may carry out functions for identifying a change in one or more characteristics of the induced cavitation bubble, wherein the identified change in the one or more characteristics corresponds to the one or more received reflection waves. Some example characteristics of a cavitation bubble may include the bubble's size, shape, dimensions, position, and velocity, among other characteristics. Furthermore, a cavitation bubble's characteristics may include a rate in which the size, shape, dimensions, position, and/or velocity are changing at a given point in time. Other possible characteristics may exist as well.

In some instances, a detection wave may reflect from a cavitation bubble having a set of characteristics, thereby producing a reflection wave. The detection wave may have a predetermined amplitude, frequency, and phase, among other wave characteristics. The reflection wave may have a different amplitude, frequency, and/or phase depending on the characteristics of the bubble. As one example, a detection wave reflecting from a bubble moving away from a probe may produce a reflection wave having a lower frequency. The characteristics of a cavitation bubble may cause a reflection wave to have different wave characteristics than the originally produced detection wave. In other words, the change of wave characteristics from the detection wave to the reflection wave may be indicative of one or more characteristics of the induced cavitation bubble.

As a general matter, computing devices may identify a change in one or more characteristics of the induced cavitation bubble by analyzing the reflection waves. As noted above, reflection waves reflecting from a bubble may have different characteristics than the detection waves produced toward the bubble. Such differences may help, facilitate, and/or aid in generating an image of the bubble. In particular, various measurements of the reflection waves may indicate characteristics of the bubble. For example, a variance in the reflection waves may be measured. In further examples, bubbles may be driven into oscillation and the oscillation may be determined by measuring phase variability, amplitude, and/or harmonics associated with the reflection waves. Thus, by determining the oscillation, the presence of the cavitation bubble, or other characteristics of the cavitation bubble, an image may be generated indicative of those characteristics.

Identifying a change in the characteristics of the induced cavitation bubble may include comparing characteristics of the emitted detection waves to characteristics of the received reflection waves. In some instances, the detection waves have a known amplitude, frequency, and phase. The received reflection waves may have an amplitude, frequency, and phase that differ from that of the emitted detection waves. Each received reflection wave may have different characteristics over time, which may indicate changes in the cavitation bubble's characteristics over time. Identifying these characteristics may require processing the analog signal, or it may require digitizing the signal using an analog-to-digital converter (ADC) or the like. The received reflection waves may be filtered, so as remove undesired noise from other sources.

A wave reflecting from a stationary object may have very similar wave characteristics to the originally produced wave. Alternatively, a wave reflecting from a cavitation bubble may have different wave characteristics than the originally produced wave. These different wave characteristics may be indicative of a variety of characteristics of the cavitation bubble. For example, a bubble that is shrinking may reflect waves at a lower frequency compared to its corresponding detection wave. A variety of other bubble characteristics may contribute to changes in wave characteristics when a wave reflects from the bubble. Whatever the characteristic may be, a wave reflection from a cavitation bubble may produce a nonlinear response, such that identifying a change in one or more characteristics is indicative of a cavitation bubble. Further, computational processing may aid in identifying the nonlinearity of the response associated with the change in characteristics of the cavitation bubble. In some instances, the vibratory wave and the detection waves may also be configured to aid in identifying the nonlinearity of the response associated with the change in characteristics of the cavitation bubble. For example, a Pulse Inversion Doppler (PID) pulse sequence (described later in more detail) may reduce the amplitude of linear responses to increase the sensitivity in identifying the change in characteristics of the cavitation bubble.

e. Generating an Image of the Cavitation Bubble

As noted for block 510 of FIG. 5, based on the identified change in the one or more characteristics, the computing device may carry out functions for generating an image of the induced cavitation bubble. The generated image may be displayed on a liquid crystal display (LCD), a plasma display, a cathode-ray tube (CRT) display, or the like. The generated image may also be stored onto a storage device as data and/or as an image that may be later displayed, printed, or otherwise made observable.

Generating the image of the cavitation bubble may include mapping received data from the reflection waves to a location in a two-dimensional (2D) space. This mapping may then be translated onto a 2D display to thereby provide spatial information about the cavitation bubble. In one embodiment, the image of the cavitation bubble is overlaid on top of a B-mode image, such that the cavitation bubble is displayed and its location is observable in relation to the medium in which it resides.

In some instances, the cavitation bubble's characteristics may be represented on the generated image. As one example, a detection wave may reflect from the cavitation bubble, and the reflected wave may return having a different frequency than that of the detection wave. In this example, the frequency shift may be represented on the display as a color. For example, if the reflection waves have a higher frequency than the detection waves, the generated image may display that frequency shift as a blue. Alternatively, if the reflection waves have a lower frequency than the detection waves, the generated image may display that frequency shift as a red. Other frequency-color mappings may exist and still produce the desired effect. In other instances, changes in phase or amplitude may be depicted in the generated image in a similar manner as previously described frequency shift. In yet another example, mappings may exist that correlate amplitude, frequency, phase, or any combination thereof to a specific color or color attribute.

4. EXAMPLE PULSE SEQUENCE VARIATIONS

A variety of pulse sequences may be implemented in order to generate an image of cavitation bubbles. A pulse sequence refers to a specific set of characteristics and timing parameters of the vibratory waves and the detection waves. Some example characteristics include amplitude, frequency, phase, pulse duration, peak pressure (positive and negative), and number of cycles, among other possibilities. Some examples of timing parameters include pulse repetition frequency of the vibratory wave, pulse repetition frequency of the detection waves, and a separation in time between the vibratory wave and the detection waves, among other possibilities. The following sections describe four example pulse sequence variations.

a. Color Doppler

Figure 7A:
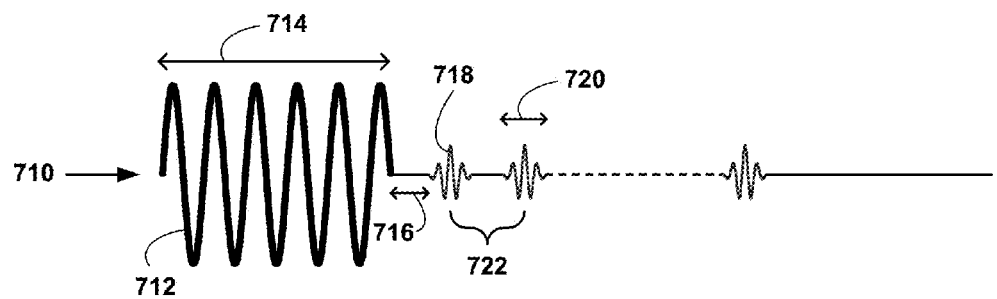
FIG. 7A depicts aspects of a Color Doppler pulse sequence associated with a computing device in accordance with one or more example embodiments.

In some embodiments, a method for imaging a cavitation bubble may utilize a Color Doppler pulse sequence. FIG. 7A depicts an example Color Doppler pulse sequence 710. A Color Doppler pulse sequence may include a vibratory wave 712 and one or more detection waves, such as detection wave 718. The vibratory wave 712 may, for example, be implemented as a high-intensity focused ultrasound (HIFU) wave. The detection wave 718 may be implemented as an acoustic pulse having an amplitude that is smaller than vibratory wave 712.

In one aspect, the vibratory wave 712 may have a pulse duration 714 ranging from 10 microseconds to 100 milliseconds, among other pulse durations. Shorter pulse durations may be preferred for inducing fewer cavitation bubbles, whereas longer pulse durations may be preferred for inducing a greater number of cavitation bubbles. The frequency of vibratory wave 712 may range from 100 kHz to 10 MHz, among other frequencies. Higher frequencies may be induce smaller cavitation bubbles, whereas lower frequencies may induce larger cavitation bubbles. The peak positive pressure created by the vibratory wave 712 may range from 2 to 150 MPa, and the peak negative pressure created by the vibratory wave 712 may range from −2 to −150 MPa, among other peak positive and negative pressures. Higher peak pressure ranges may be adjusted depending on the sensitivity of the technique used to detect and measure the reflection waves, whereas lower peak pressure ranges may provide a safer pressure level depending on the application of the vibratory wave. The vibratory wave 712 may be repeated at a pulse repetition frequency ranging from 1 Hz to 20 kHz, among other pulse repetition frequencies. A higher pulse repetition frequency may induce new cavitation bubbles and/or to interact with previously induced cavitation bubbles more frequently. Further, a lower pulse repetition frequency may induce new cavitation bubbles less frequently and/or interact with previously induced cavitation bubbles. All such wave characteristics previously described may also be varied for other benefits or purposes that are not expressly stated herein.

In one embodiment, the Color Doppler pulse sequence includes period of time 716 between the vibratory wave and the first detection wave. This period of time 716 may range from 10 microseconds to 100 microseconds, among other lengths of time. In one aspect, the vibratory wave 712 induces the cavitation bubbles, and subsequently the produced vibratory wave 712 causes backscatter. The resulting backscattering of the vibratory wave 712 may be detected by a probe or sensor configured to detect the backscattering of the detection waves reflecting from the induced cavitation bubbles. In some instances, the detected backscattering from the vibratory wave is a broadband signal having a large amplitude, which may saturate a sensor and dominate subsequent any readings from a probe or sensor until the dissipation of the backscattering. The period of time 716 may be configured such that the detection waves are transmitted after significant attenuation of the backscattering resulting from the vibratory wave 712.

In one aspect, the detection wave 718 may include 1 to 10 cycles, among other numbers of cycles. The detection wave 718 may also be repeated at a pulse repetition frequency ranging from 1 Hz to 20 kHz, among other pulse repetition frequencies. Other characteristics of detection wave 718, such as the characteristics described above with respect to vibratory wave 712, may be varied.

In one example, vibratory wave 712 is a HIFU wave, and detection wave 718 is an acoustic wave. In this example, both the vibratory wave 712 and the detection wave 718 may be produced using a transducer or an array of transducers. Vibratory wave 712 may be an acoustic wave having a frequency that is above or below the ultrasound range, or alternatively vibratory wave 712 may be an electromagnetic wave such as a radio-frequency (RF) pulse, a microwave pulse, or an optical pulse. The detection wave 718 may also take on similar forms to that of vibratory wave 712.

A Color Doppler pulse sequence may be desired for a variety of reasons. For instance, the pulse repetition frequency 722 may be set to be a high frequency, such that each detection wave 718 is separated by a short period of time. In this instance, each reflection wave reflecting from the cavitation bubbles may return in rapid succession, thus enabling the reading of a set of data about the characteristics of the cavitation bubbles as they change over a short period of time. Measuring the changes in the characteristics of the cavitation bubbles between each repetition of detection wave 718 may be referred to herein as detecting the changes in "fast time." In one example, the cavitation bubbles are induced by vibratory wave 712. After the vibratory wave 712 stops, the cavitation bubbles may begin to decrease in size and/or collapse. A rapid succession of detection waves 718 may be used in determining these changes in the cavitation bubbles over time.

b. Pulse Inversion Doppler

Figure 7B:
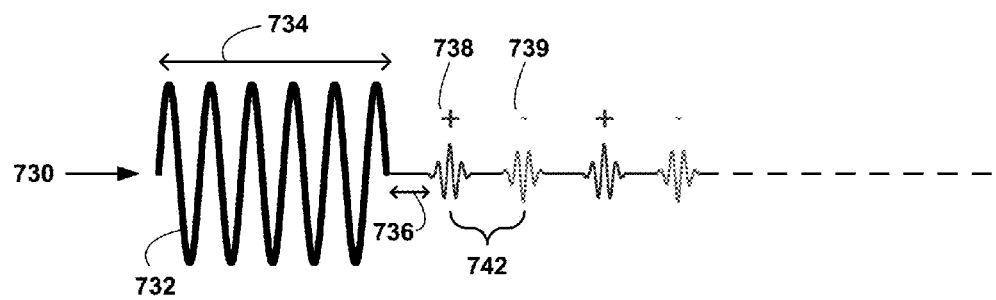
FIG. 7B depicts aspects of a Pulse Inversion Doppler pulse sequence associated with a computing device in accordance with one or more example embodiments.

In some embodiments, a method for imaging a cavitation bubble may utilize a Pulse Inversion Doppler pulse sequence. FIG. 7B depicts an example Pulse Inversion Doppler pulse sequence 730. A Pulse Inversion Doppler (PID) pulse sequence may include a vibratory wave 722 and one or more detection waves, such as positive-phase detection wave 738 and negative-phase detection wave 739. Negative-phase detection wave 739 may be an inversion of the positive-phase detection wave 738, but otherwise may have similar characteristics. In one example, the negative-phase detection wave 739 and the positive-phase detection wave 738 have a phase difference of approximately 180 degrees (i.e. in opposite phase or anti-phase). The positive-phase detection wave 738 and negative-phase detection wave 739 may be repeated at a pulse repetition frequency 742, and the repetition may alternate from the positive-phase detection wave 738 to negative-phase detection wave 739. Wave characteristics of vibratory wave 732 may be similar to that of vibratory wave 712, and wave characteristics of positive-phase detection wave 738 and negative-phase detection wave 739 may be similar to that of detection wave 718. Note that the "+" displayed above the positive-phase detection wave 738 and the "−" displayed above the negative-phase detection wave 739 are for illustrative purposes only.

A PID pulse sequence may be desired for a variety of reasons. For instance, the positive-phase detection wave 738 and negative-phase detection wave 739 may be configured such that the combination of two reflection waves resulting from the two detection waves reflecting from the cavitation bubbles only contains the second harmonic of the two detection waves. The second harmonic of the detection waves may be associated with the nonlinear backscattering used to detect the characteristics of the cavitation bubbles.

c. Interleaving Doppler

Figure 7C:
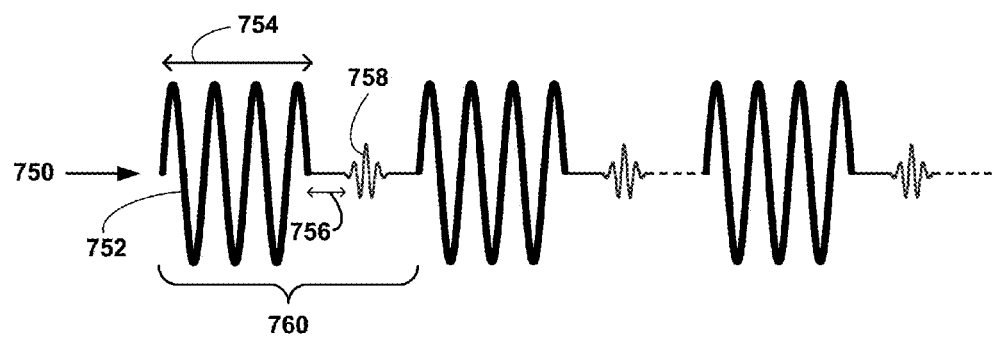
FIG. 7C depicts aspects of a Interleaving Doppler pulse sequence associated with a computing device in accordance with one or more example embodiments.

In some embodiments, a method for imaging a cavitation bubble may utilize an Interleaving Doppler pulse sequence. FIG. 7C depicts an example Interleaving Doppler (ID) pulse sequence 750. An ID pulse sequence may include vibratory waves, such as vibratory wave 752, and detection waves, such as detection wave 758. In one instance, the ID pulse sequence may alternate between producing vibratory waves, such as vibratory wave 752, and detection waves, such as detection wave 758, the combination of which may be referred to herein as an "interleaving wave pair." The interleaving wave pair may be repeated at a pulse repetition frequency 760. The vibratory wave 752 and the detection wave 758 may be separated by a period of time 756 that is similar in length to period of time 716. Wave characteristics of vibratory wave 752 may be similar to that of vibratory wave 712, and wave characteristics of detection wave 758 may be similar to that of detection wave 718. In one example, the vibratory wave 752 has a shorter pulse duration 754 relative to vibratory wave 732 and vibratory wave 712.

An Interleaving Doppler pulse sequence may be desired for a variety of reasons. For instance, the first vibratory wave 752 may induce the cavitation bubbles in a medium, and subsequent vibratory waves may interact with the previously induced cavitation bubbles and/or induce new cavitation bubbles. As a result, each successive vibratory wave may significantly change the distribution, number, and characteristics of the cavitation bubbles. The significant fluctuations may allow for decreased peak pressures while providing adequate cavitation bubble fluctuations to be measured.

d. Bubble Doppler

Figure 7D:
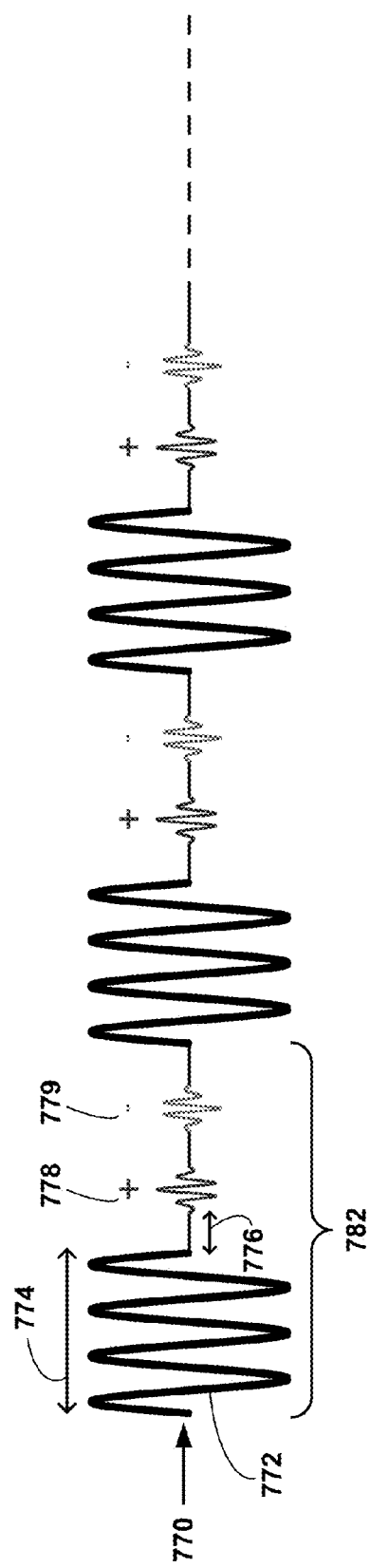
FIG. 7D depicts aspects of a Bubble Doppler pulse sequence associated with a computing device in accordance with one or more example embodiments.

In some embodiments, a method for imaging a cavitation bubble may utilize a Bubble Doppler pulse sequence. FIG. 7D depicts an example Bubble Doppler (BD) pulse sequence 770. A BD pulse sequence 770 may include vibratory waves, such as vibratory wave 772, and one or more detection waves, such as positive-phase detection wave 778 and negative-phase detection wave 779. Positive-phase detection wave 778 may be similar to that of positive-phase detection wave 738, and negative-phase detection wave 779 may be similar to that of negative-phase detection wave 739. Vibratory wave 772 may be similar to that of vibratory wave 752. In one example, the BD pulse sequence 770 incorporates the repeating of vibratory wave 772, similarly to the ID pulse sequence 750, and the alternating of the positive-phase detection wave 778 and negative-phase detection wave 779, similarly to the PID pulse sequence 730.

A BD pulse sequence may be desired for a variety of reasons. For example, by combining aspects of the ID pulse sequence 750 and the PID pulse sequence 730, imaging the induced cavitation bubbles may be achieved with greater sensitivity compared to other pulse sequences. Additionally, a BD pulse sequence may be implemented using existing ultrasound systems, and does not necessarily require new probes or transducers.

Note that, in FIG. 7A, FIG. 7B, and FIG. 7C, the waves as shown are not drawn to scale and do not represent any particular amplitude, frequency, pulse repetition frequency, phase, or any relation to actual timing. Also note that the pulse sequences only depict one set of pulses; any of the pulse sequences may be repeated with the same wave characteristics and timing parameters or different wave characteristics and timing parameters, depending on the desired result. The drawings are merely representative of the pulse sequences generally, and are shown for purposes of explanation.

5. CLINICAL APPLICATIONS

The examples discussed hereafter are for purposes of illustrating how the subject matter of the present application may be implemented for different applications, such as for medical and/or diagnostic applications. In particular, the examples discussed hereafter provide illustrations regarding possibly ways to implement and utilize features described in this application. The following examples are not meant to be limiting or restrictive of the scope of the present application. Additionally, the following examples may implement any pulse sequence, such as the previously described pulse sequences, depending on the desired effect, among other pulse sequences. Furthermore, the following applications described below pertain to human subjects, although the method may also be applied to mammalian subjects as well.

In one instance, the method of imaging cavitation bubbles may be administered to a subject or patient having a primary or metastatic tumor. In some instances, a patient's tumor may not respond to chemotherapy as a result of a lack of penetration of the drug into the tumor. As one example, a vibratory wave such as a HIFU wave may be applied to the tumor of interest, thereby inducing cavitation bubbles in the tumor. Subsequent HIFU waves may be administered to interact with the cavitation bubbles, the fluctuation of which causes a mechanical disruption within the tumor and may lead to increased permeabilization of the blood vessels inside the tumor. As a result, chemotherapeutic drug penetration may increase, leading to a more effective chemotherapeutic treatment. The method may be applied simultaneously or in tandem with the administration of a chemotherapeutic agent. Generating an image of the cavitation bubbles during chemotherapy may provide useful feedback to a technician, nurse, or doctor administering the ultrasound pulses so that he/she may monitor the progress of the chemotherapy and/or make adjustments to the ultrasound pulses to achieve a desired effect. This method of imaging cavitation bubbles may also be applied to similar techniques that utilize HIFU waves to increase permeabilization in other tissues requiring increased drug penetration; one such example includes techniques intended to increase drug penetration through a blood-brain barrier of a patient in order to increase the efficacy of a treatment for a neurological disorder. In this example, imaging the cavitation bubbles may be desired for monitoring the progress of such treatment.

This method may also be administered to a patient with a tumor for other purposes. For example, if an unidentified mass is observed inside of a patient, a pulsed ultrasound may be directed toward the mass in order to stimulate the release of biomarkers. A blood sample may then be drawn to determine if the unidentified mass released cancer-specific biomarkers during the pulsed ultrasound. The method of imaging cavitation bubbles may be useful for a technician, nurse, or doctor administered the pulsed ultrasound so that he/she may monitor the progress of the cavitation action on the unidentified mass and/or make various adjustments to the location, depth, and other characteristics of the ultrasound pulses to achieve a desired effect.

In another instance, the method of imaging cavitation bubbles may be administered to a patient suffering from an orthopedic condition. Some examples of orthopedic conditions include bone loss, plantar fasciitis, tennis elbow, and wound healing, among others. In this instance, treatment of the orthopedic condition may incorporate the mechanical fluctuations of cavitation bubbles in the tissue surrounding a bone. Such a treatment, however, may require real time or near-real time feedback in order to adjust the wave parameters to improve the efficacy of the treatment. Using the present method, a technician, nurse, or doctor administering an ultrasound therapy to treat an orthopedic condition can view a generated image of the cavitation bubbles and make adjustments to the location, depth, wave characteristics, and other parameters based on the image.

Other such clinical applications may exist. In some instances, monitoring the cavitation bubbles may be desired in order to detect excess cavitation activity, so as to avoid unintentionally ablating tissue within a patient. Tissue may be heated too excessively or damaged as a result of excess cavitation activity, such as during HIFU hyperthermia treatments or burst wave lithotripsy (BWL) if the cavitation activity is not monitored and controlled. In some instances, it may be desired to halt an ultrasound therapy if such excess cavitation activity is detected.

6. ADDITIONAL IMPLEMENTATIONS, APPLICANTS, AND EXAMPLES

The Examples that follow are illustrative of specific embodiments of the invention, and various uses thereof.

They are set forth for explanatory purposes only, and are not to be taken as limiting the invention.

a. Example A: Gel Phantom

In the following example, various pulse sequences and the imaging of induced cavitation bubbles are performed on a gel phantom.

MATERIALS AND METHODS

Experimental Setup

Figure 8:
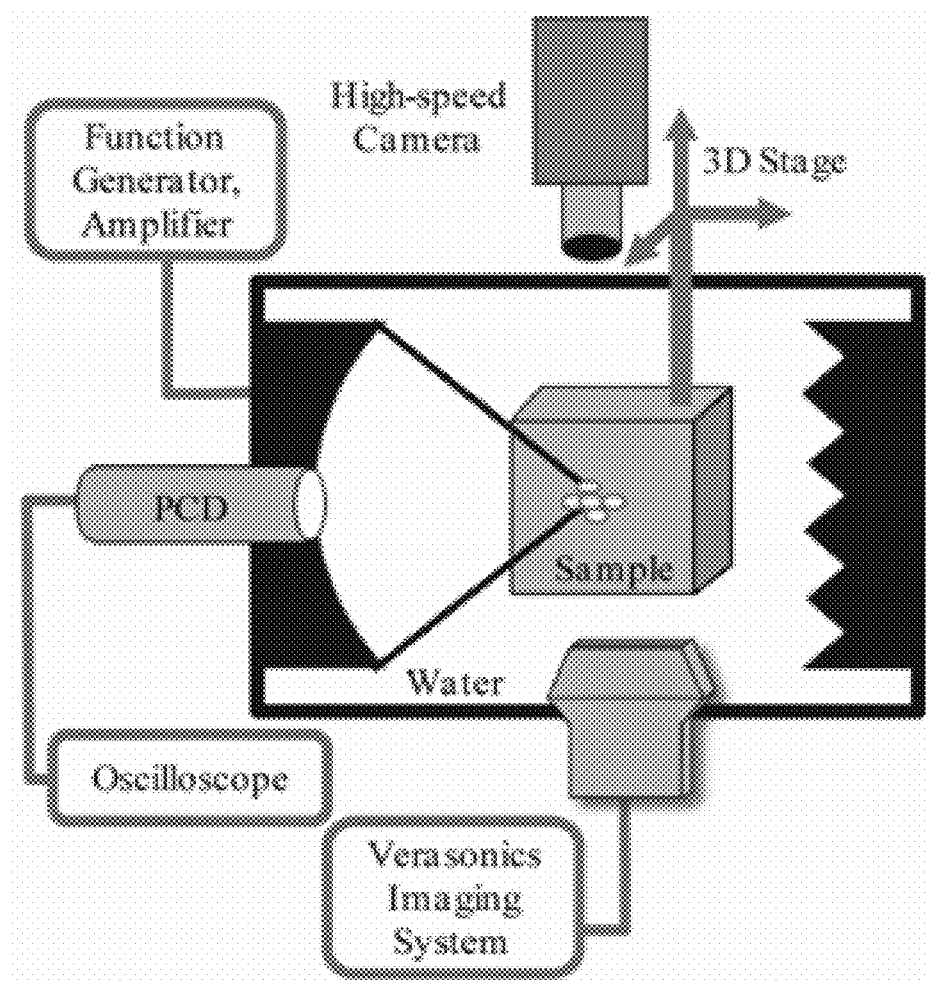
FIG. 8 depicts a schematic illustration of an experimental setup in accordance with one or more example embodiments.

The experimental setup used in this study is shown in FIG. 8. The pHIFU exposures were performed in an acrylic water tank filled with purified water degassed to 25-28% oxygen saturation, as measured by a dissolved oxygen meter. All of the pHIFU exposures were performed by a 1.27-MHz spherically focused transducer with 64 mm aperture and 64 mm radius of curvature, and a central circular opening of 22 mm in diameter. The HIFU transducer was powered by a computer-controlled combination of an RF amplifier and a function generator. Before the experiments, the focal pressure waveforms produced by the transducer in water at the different power levels were characterized by a fiber optic probe hydrophone. To vary the amounts of induced cavitation activity and to determine cavitation thresholds, the focal peak negative HIFU pressure was varied within the range of 0.9-11 MPa, with a step size of 0.5 MPa.

A focused 5 MHz PCD transducer with 19 mm diameter and 49.5 mm focal length was fitted into the circular opening of the HIFU transducer and aligned confocally with the HIFU transducer, as shown in FIG. 8. The dimensions of the focal areas for HIFU and PCD are 12 mm×1.6 mm and 55 mm×2 mm at −6 dB level, respectively.

Figure 9:
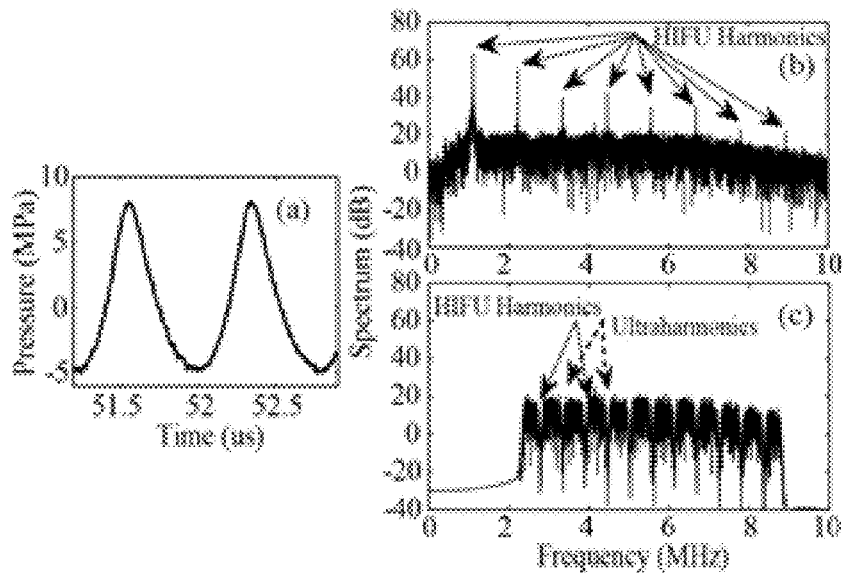
FIG. 9 depicts example waveforms in accordance with one or more example embodiments.

For ultrasound imaging of the HIFU exposures, the Verasonics Ultrasound Engine was used, with a clinical linear imaging probe ATL/Philips HDI L7-4 consisting of 128 elements. FIG. 9 shows the probe was aligned perpendicularly to the HIFU transducer axis as shown. On the opposite side of the clinical probe, a Photron APX-RS high-speed camera was placed to visually observe and record bubble activity at the HIFU focus. The high speed camera was set to a frame rate of 30 k frames/s, a resolution of 256×512 pixels.

Gel Phantoms

To make optical observation of bubble activity possible, all the studies were performed in transparent PA (7% w/v) phantoms[1,2,3]. The gel was added with 7% w/v bovine serum albumin (BSA) to serve as an indicator for any thermal denature. To prepare the samples, the liquid mixture of PA gel constituents was degassed for 1 hour in a desiccant chamber by a vacuum pump. The degassed mixture was poured into a custom mold (5 cm wide by 5 cm tall by 8 cm deep). The polymerization was then initiated by the addition of a 10% (w/v) ammonium persulfate solution and N,N,N', N'-tetra-methylethylene/diamine. After the PA gel phantom was set, it was placed in to a custom designed holder. The holder had four side openings to provide both acoustic and optical window for observation. The acoustic absorber was attached to the wall of the water tank opposite the HIFU transducer to reduce reverberation. The gel phantom was positioned so that HIFU focus was 15 mm deep below the gel surface.

PCD Signal Processing

During the HIFU exposures, a series of 1 ms duration broadband signals were acquired by the PCD transducer and processed using a custom-made digital filter using MATLAB as described in our previous stud?. Since the majority of the focal HIFU waveforms used in this study were nonlinearly distorted (FIG. 9(*a*)), the backscattered harmonics of the HIFU wave dominated the band-pass filtered PCD signal. FIG. 9(*b*) shows an example of the frequency spectrum of the signal recorded by the PCD. A combination of a band-pass filter (Matlab function fir1) and a notch-shaped comb filter (Matlab function iirnotch) was used to separate the frequency components associated with the broadband noise emissions of inertially collapsing bubbles (FIG. 9(*c*)). The filtered PCD signal was further analyzed in time domain to obtain a binary evaluation metric of whether a cavitation event took place within the HIFU pulse duration. The cavitation event was considered observed if the signal amplitude exceeded the maximum amplitude of the background noise by a factor of $\sqrt{5}$—the Rose criterion. This binary measure was obtained for the pHIFU exposures performed at each of the peak negative pressure levels. At each level, 20 different spots in the gel phantom were treated. We then calculated cavitation probability at each level as the ratio (expressed in percent) of the number of pHIFU focus locations, at which at least one cavitation event was observed throughout the exposure, to the total number of spots treated. Similarly to our previous work, the cavitation threshold was defined as the peak negative pressure level corresponding to 50% of cavitation probability.

Ultrasound Imaging

The imaging was performed in a "flash" transmitting mode when all the array elements were excited simultaneously to emit a quasi-plane wave in the direction orthogonal to the radiating surface at zero degrees incident angle. Color Doppler imaging was followed by B-mode imaging. In the Doppler mode, the central 64 elements were excited by a series of 14 Doppler ensemble pulses (the default number of pulses for VUE) emitted with a pulse repetition frequency (PRF) set through VUE flash mode color Doppler programmable script[5]. The event sequences of the VUE script was modified so that Doppler pulses were transmitted following HIFU pulses. Each Doppler pulse was a 3-cycle pulse with 5 MHz central frequency with the pressure levels of $P^+=2$ MPa and $P^-=1$ MPa[6]. In the B mode, all the 128 elements were excited by a single-cycle 5 MHz pulse. The received signals in both Doppler and B mode regimes were sampled at 20 MHz frequency by a 12-bit analog-to-digital convertor (ADC) and saved in the receive buffer of VUE. The saved raw radio-frequency (RF) signals were later used for Doppler processing and image reconstruction.

It is important to note that, of the 14 Doppler ensemble pulses, the first two pulses are omitted to avoid possible unrepeatable tissue reverberation. The later 12 pulses were used in further Doppler processing and image reconstruction. Therefore, further in the text the third transmitted Doppler pulse will be referred to as the first Doppler pulse.

Figure 10:
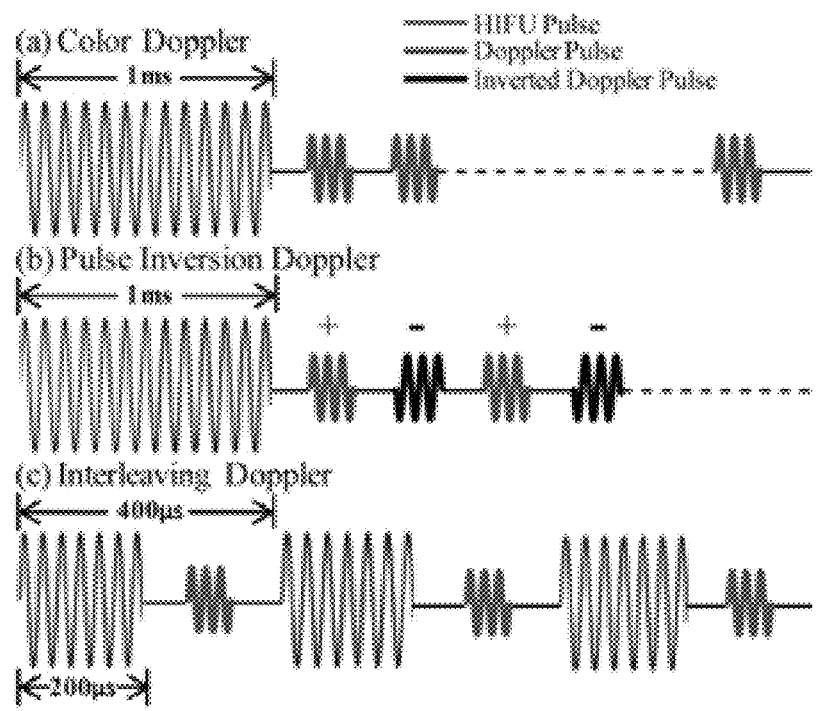
FIG. 10 depicts example pulse sequences in accordance with one or more example embodiments.

In this study, three different pulse sequences were used for synchronizing the HIFU pulses with the Doppler ensemble that are illustrated in FIG. 10. The first sequence will be referred to as Color Doppler sequence (FIG. 10(*a*)). A series of twenty 1-ms HIFU pulses were delivered at a PRF of 1 Hz to a single treatment location in the sample. This HIFU pulsing scheme was chosen to match our previous work on measurement of the cavitation threshold in tissues and phantoms and chemotherapeutic drug delivery to pancreatic tumors[4,7]. Immediately after each HIFU pulse ended, a series of 12 Doppler ensemble pulses were transmitted and received by the imaging probe in flash mode with a PRF of 3 kHz. This PRF was chosen because it is typical for the Doppler regimes in clinical ultrasound machines. The received Doppler ensemble pulses were then both stored for off-line processing and also used in real time to form a Color Doppler image. Immediately after transmitting and receiving the Doppler pulses, a 1-cycle 5 MHz pulse was transmitted in a flash mode and received by the imaging probe to form a B-mode image, which was then combined with the Color Doppler image. After 20 sets of pulses (consisting of one HIFU pulse, 12 Doppler pulses and one B mode pulse) were transmitted, the focus location was moved to a different location in the phantom.

The second pulse sequence—PID—was identical to Color Doppler, with one modification: every other pulse in the Doppler ensemble following the HIFU pulse was inverted, as shown in FIG. 10(*b*). This sequence allows to separate the Doppler spectrum that contains In this sequence the Doppler spectrum contains only Doppler signals arising from non-linear scattering processes, in particular—the second harmonic of the transmit signal[8]. Since the frequency band of the imaging probe was 4-7 MHz, the transmit frequency was set to 3 MHz so that the second harmonic (6 MHz) would be within the frequency band of the transducer.

The third pulse sequence will be referred to as Interleaving Doppler and is illustrated in FIG. 10(*c*). Twenty sets of pulses, each consisting of 12 HIFU pulses interleaved with 12 Doppler ensemble pulses were delivered to a single treatment spot at a PRF of 1 Hz. Each HIFU pulse was reduced in duration down to 200 µs compared to the first two pulse sequences in order to keep the Doppler pulse PRF nearly the same—2.5 kHz. The Doppler pulse was transmitted after the HIFU signal stopped transmitting to avoid interference. Similarly to the Color Doppler and Interleaving Doppler sequences, one Doppler image was reconstructed from 12 Doppler pulses. Right after each set of the interleaved HIFU pulses and Doppler pulses were delivered, a single 1-cycle 5 MHz signal was transmitted and received to form a B-mode image.

Signal Processing

Figure 11:
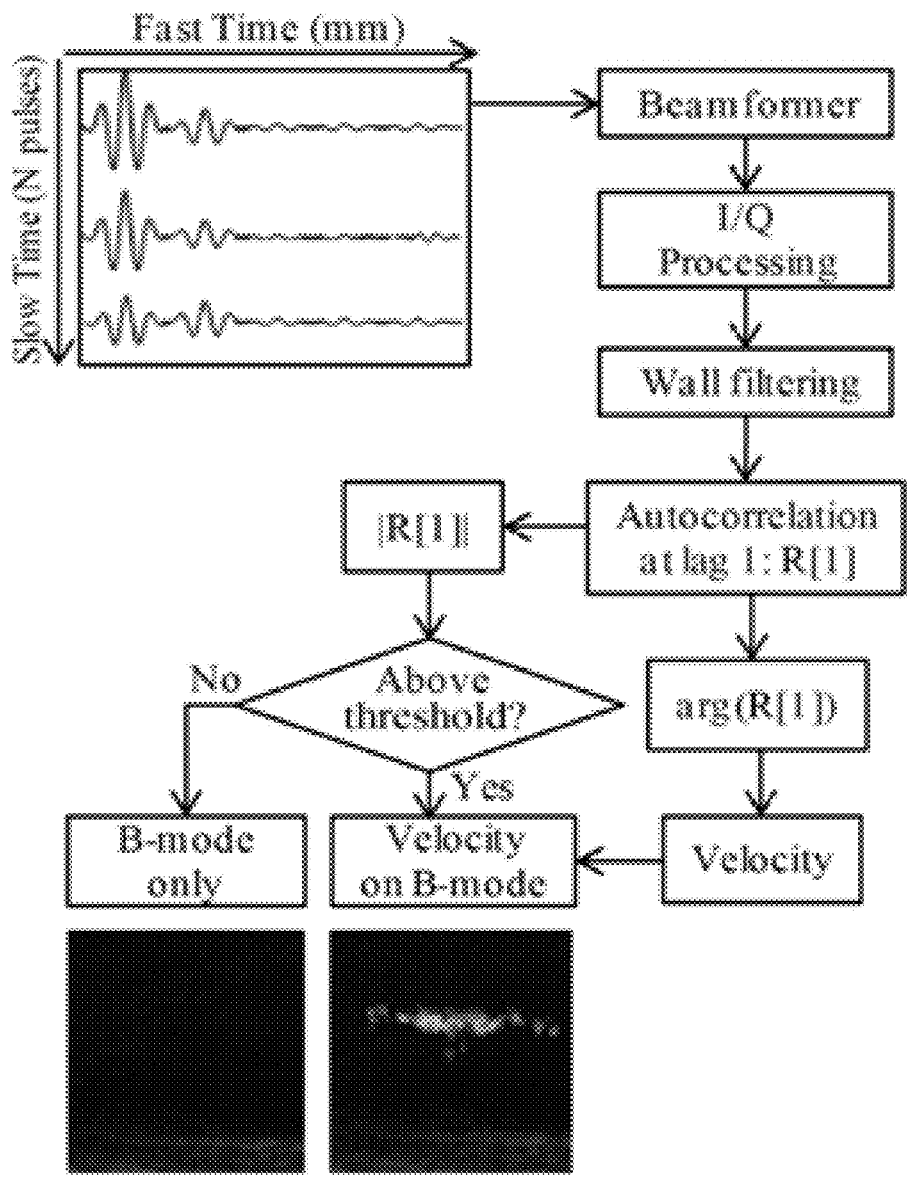
FIG. 11 depicts a flow diagram of example Doppler signal processing in accordance with one or more example embodiments.

After the experiments, the raw RF signals were analyzed in Matlab (MATLAB 2010b, The MathWorks, Natick, Mass., USA) to reconstruct Doppler images according to the algorithm illustrated in FIG. 11. Consider a Doppler ensemble consisting of N=12 pulses. The time from one transducer firing to the next is defined as "slow time", and is denoted as the number of the pulse within the Doppler ensemble, i. The time elapsed during reception of each pulse is defined as "fast time", t, and is determined by the round-trip time of flight of a Doppler pulse and measured in millimeters: 2 l=ct where c is the speed of sound. The received RF signals were first beamformed by using the conventional "delay-and-sum" method. Consider the received beamformed echo signal E(n), which can be represented as $E(n)=R_e\{Z(n)e^{j\omega_o n}\}$, where Z(n) is the complex envelope of the E(n), n is the sample point and $\omega_o$ is the angular central frequency of the signal[9]. By using a quadrature detector, the real and imaginary parts of Z(n) could be separately obtained. In this case, Hilbert transform was used as a quadrature detector.

Next, wall filtering (first order regression filter) was applied to the complex, beamformed signals along slow time to remove the signals from stationary or slowly moving scatterers and separate only Doppler residuals[10]. In the PID case, an additional low pass filter along slow time was applied to remove the signals associated with the linear scatterers. The cut-off frequency of the filter was PRF/4 (Matlab function sgolayfilt).

After wall filtering, we used the most common method for velocity and Doppler power estimation in modern systems, the autocorrelation algorithm[9]. Let P(ω) be the Doppler power spectrum; the mean Doppler frequency shift $\bar{\omega}$ is then defined as:

$$\bar{\omega} = \frac{\int_{-\infty}^{\infty} \omega P(\omega) d\omega}{\int_{-\infty}^{\infty} P(\omega) d\omega}$$

The mean velocity can be then derived as follows:

$$\bar{v} = \frac{\bar{\omega} c}{\omega_o 2 \cos\theta}$$

where $\omega_o$ is the angular frequency of the carrier signal, θ is the angle between the sound beam and the direction of the flow.

Let R(k) be the Doppler autocorrelation function along slow time:

$$R(k) = \sum_{i=1}^{N} Z(i) Z^*(i+k)$$

where N is the total number of Doppler pulses along slow time and i is the number of the pulse in the Doppler ensemble. By the Wiener-Khinchine's theorem, the following relationship pertains between R(k) and P(ω):

$$R(k) = \int_{-\infty}^{\infty} P(\omega) e^{j\omega k} d\omega$$

According to Kasai et al., the mean Doppler frequency shift $\bar{\omega}$ can be calculated as the phase of the autocorrelation function at a lag of one Doppler pulse repetition period, arg R(1):

$$\bar{\omega} = \arg \Sigma_{i=1}^{N-1} Z(i) Z^*(i+1)$$

Doppler power is calculated as |R(1)|. Thus, both Doppler frequency shift and Doppler power at each fast time sampling point were calculated using this approach. At the final step, the Doppler power at each pixel of the image was compared to a threshold, and if it exceeded the threshold, color Doppler information, i.e. the phase of R(1), was displayed on top of B-mode pixels. The threshold was defined the same way as in Lu et al.[6]: the background noise level, defined as the average of the Doppler powers over all pixels in the image, multiplied by the factor of two.

Results

Pilot Observations with High Speed Camera and Color Doppler Ultrasound Imaging

Figure 12:
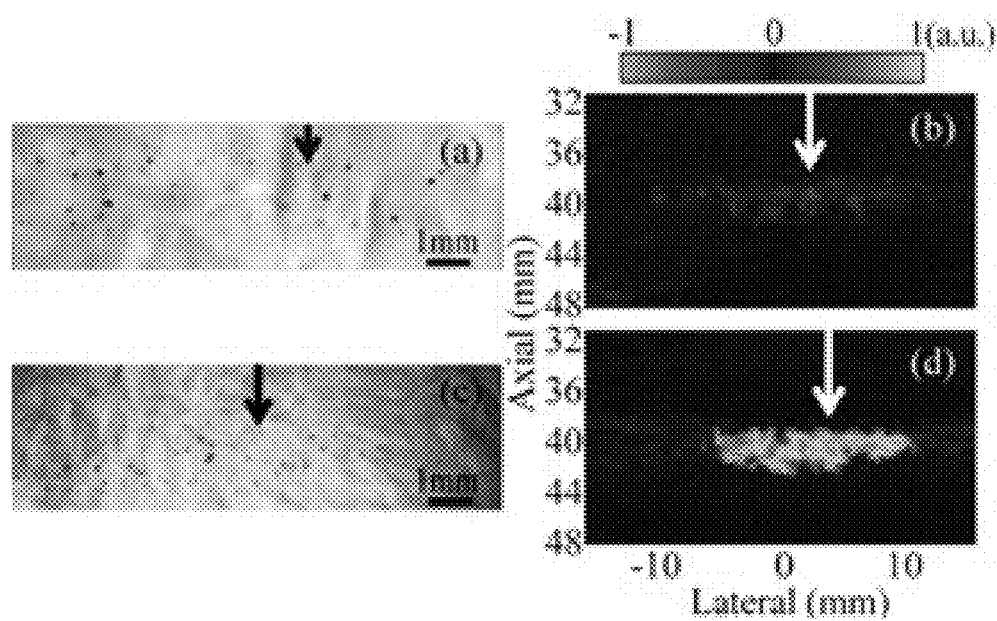
FIG. 12 depicts observations of cavitation activity in accordance with one or more example embodiments.

In the first series of experiments, simultaneous observation of pHIFU-induced bubble activity in the gel phantom was performed by the high speed camera and Doppler ultrasound using two different pulse sequences—Color Doppler and Interleaving Doppler[9]. The pHIFU focal peak negative pressure in this case was 5.1 MPa. The VUE ultrasound system was used to display color Doppler images in real time, without any further signal processing. The obtained color Doppler images of the HIFU transducer focal area are presented side by side with the corresponding high speed camera images in FIG. 12 for both pulsing sequences. The cavitation bubbles distributed throughout the transducer's oval-shaped focal area are clearly visible in both high speed camera images as dark spots (FIGS. 12(a) and 12(c)). The bubbles are somewhat smaller in the Interleaving Doppler pulse sequence (FIG. 12(c)) due to the smaller duration of the HIFU pulse in this case. The size and position of the colored region in Doppler ultrasound corresponds well to the size and position of the bubble distribution seen on the high speed camera images, providing one confirmation that the color region originates from the cavitation bubbles. In both cases, the color region grew in size with the increase of the HIFU focal peak negative pressure, and disappeared as the peak negative pressure fell below a certain threshold (3.1 MPa for color Doppler and 1.9 MPa for Interleaving Doppler).

The Doppler images corresponding to the two pulsing sequences look qualitatively different. In the Color Doppler sequence, the region displaying color contains alternating dark red and blue areas that, in Doppler processing, would be interpreted as very slowly, chaotically moving scatterers (FIG. 12(b)). In the Interleaving Doppler, the color region contains a color mosaic characteristic of the TA typically seen on hard concretions in tissue (FIG. 12(d)), and would be interpreted as scatterers having the entire range of speeds and moving in all directions at once. These qualitative characteristics were the same across the whole range of pHIFU focal pressures.

Interpretation of the Pilot Results Based on the Raw Signals

Figure 13:
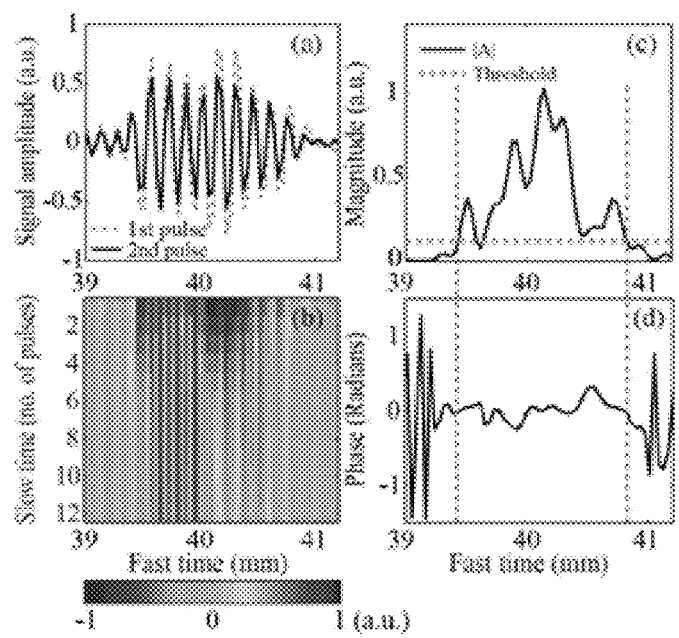
FIG. 13 depicts various representations of reflection waves associated with a Color Doppler pulse sequence in accordance with one or more example embodiments.

In order to explain the origin of the different color displays in the Color Doppler and Interleaving Doppler, the stored RF signals from the middle element of the ultrasound array were considered. FIG. 13(a) presents the first two of the Doppler ensemble pulses from the depth corresponding to HIFU focus location. As seen, the amplitude of the first pulse is larger than that of the second pulse, but there is no visible phase shift between the pulses. FIG. 13(b) shows the received signal amplitude plotted along slow time and fast time. At all of the fast time sampling points, the signal amplitude gradually declines across slow time that suggests the presence of a scatterer with decreasing reflectance. The amplitude (FIG. 13(c)) of the autocorrelation function at lag one peaks at the fast time point corresponding to the fastest decrease in signal amplitude over slow time (40.2 mm). The fast time range in which the amplitude of autocorrelation exceeds the threshold for color display (39.4-41 mm) corresponds to the autocorrelation phase (FIG. 13(d)) that fluctuates around zero, within a narrow range of −0.3-0.3 radians. These observations suggest the following mechanism for the appearance of the dark red and blue area in the Color Doppler image: pHIFU induces cavitation bubbles that gradually dissolve after the HIFU pulse is delivered. The amplitude of the backscattered Doppler pulses is strongly affected by the change in the bubble size, and therefore the amplitude of the autocorrelation at lag 1 is high, and the bubble is displayed as color. However, the signal phase does not change from one Doppler pulse to the next, because the bubbles are not moving, and the displayed speed is close to zero and is shown as dark red and dark blue color in the reconstructed image (FIG. 12(b)).

Figure 14:
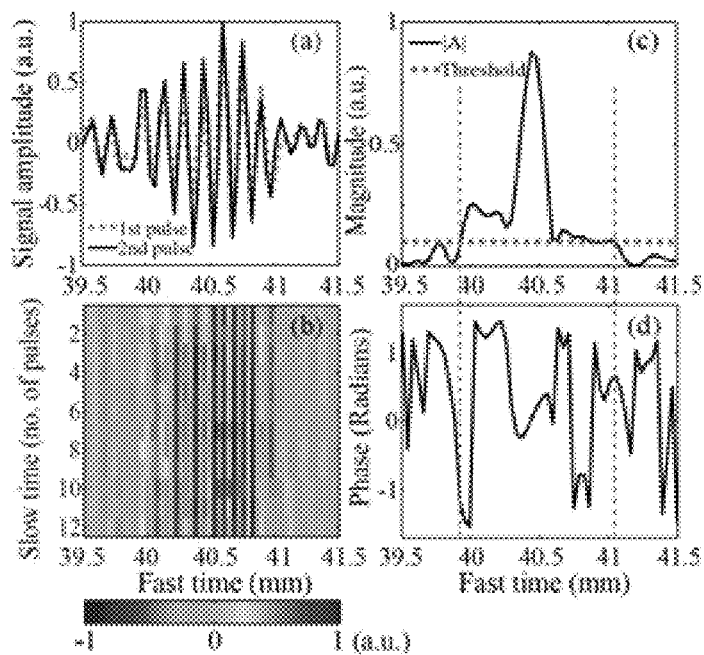
FIG. 14 depicts various representations of reflection waves associated with an Interleaving Doppler pulse sequence in accordance with one or more example embodiments.

In the Interleaving Doppler pulse sequence, the overall levels of the first two signals of the Doppler ensemble are similar (FIG. 14(a)), however, the noticeable phase shifts and relative fluctuations are present. As seen in FIG. 14(b), these fluctuations continue across the slow time suggesting that the backscattered signal from pHIFU generated bubbles changes sporadically from one Doppler pulse to the next. FIGS. 14(c) and 14(d) show that the fast time segment, at which the autocorrelation amplitude is above the threshold (39.8-41.2 mm), corresponds to phase fluctuations in the wide margins (−pi/2-pi/2). This suggests that the distribution of bubbles resulting from each HIFU pulse is different in the bubble size, number and positions. These changes induced by different HIFU pulses result in large autocorrelation amplitude and random phase changes which manifest themselves as the color mosaic in the color Doppler image.

Figure 15:
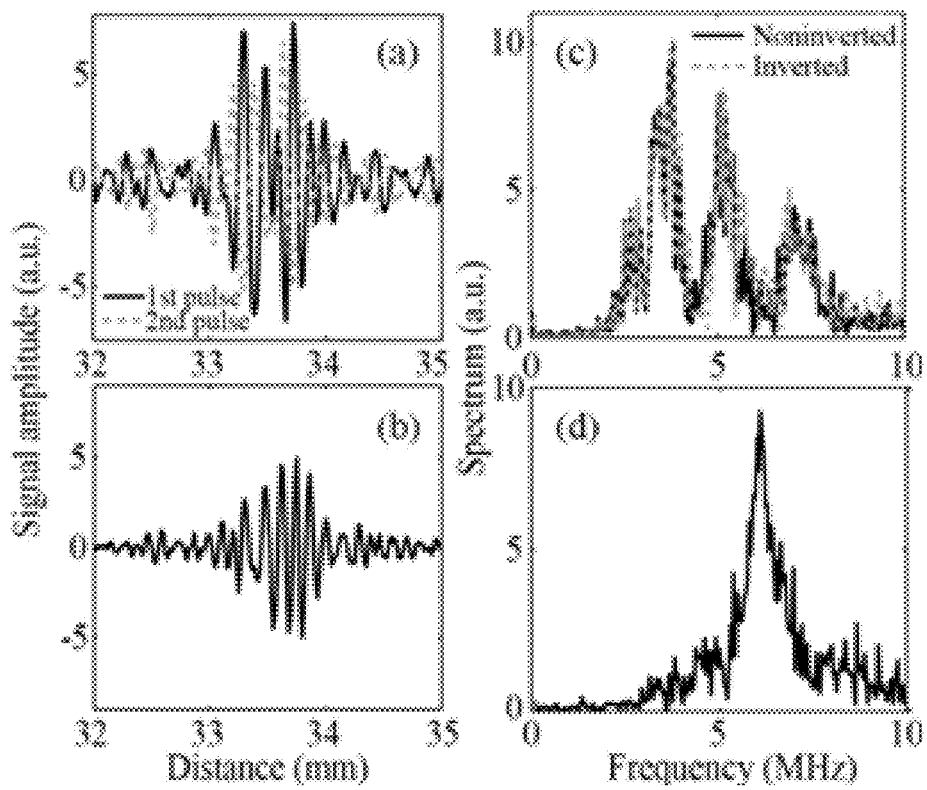
FIG. 15 depicts various representations of reflection waves associated with a Pulse Inversion Doppler pulse sequence in accordance with one or more example embodiments.

In Pulse Inversion Doppler, the sum of the inverted and non-inverted subsequent Doppler pulses only contains the second harmonic of the transmitted signal, i.e. the signal associated with the nonlinear scatterers. An example of the first two received RF signals from Pulse Inversion Doppler ensemble are shown in FIG. 15(a). The spectra of both signals (FIG. 15(b)) contain the harmonics of the center transmit frequency of 3 MHz. When the pulses are summed (FIG. 15(c)), only the second harmonic signal at 6 MHz is left in the spectrum (FIG. 15(d)). This suggests that the residual bubbles induced by the HIFU pulse produce a strong enough nonlinear response to be detectable by pulse inversion Doppler. In this particular example, the peak negative focal pressure of the HIFU pulse was 4.6 MPa.

Figure 16:
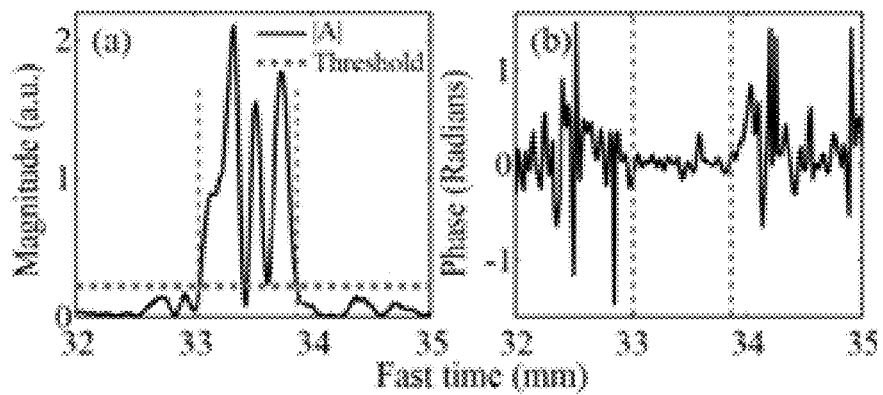
FIG. 16 depicts further representations of reflection waves associated with a Pulse Inversion Doppler pulse sequence in accordance with one or more example embodiments.

The fast time range in which the amplitude of autocorrelation function (FIG. 16(a)) exceeds the threshold for color display (33-33.8 mm) corresponds to the autocorrelation phase (FIG. 16(b)) that fluctuates around zero, suggesting that bubbles don't move from one pulse to the next but they produce nonlinear response.

Investigation of the Doppler Technique's Sensitivity

Figure 17:
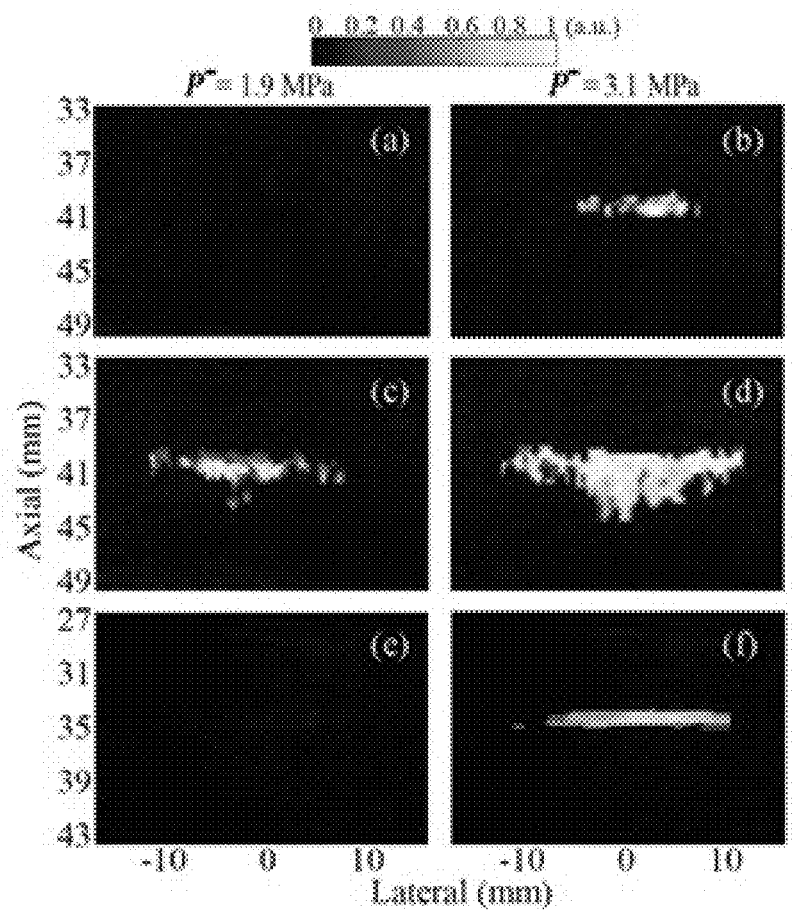
FIG. 17 depicts an example display resulting from the present method in accordance with one or more example embodiments.

The pilot experiments with all of the three pulse sequences indicated, that in all cases the increased magnitude of the Doppler signal originated from the changes in pHIFU-induced bubble distribution across slow time, or from the nonlinearity of the bubbles. However, the Doppler signal phase did not correspond to the true motion of the bubbles or reflect any of the bubble characteristics. Therefore, the phase information was discarded in the future studies, and instead Doppler signal magnitude was displayed on top of the B-mode images, i.e. Power Doppler regime, rather than Color Doppler, was implemented. The corresponding images, reconstructed offline, for all three pulse sequences at two different pHIFU power levels are shown in FIG. 17.

Based on the pilot experimental results, the three Doppler techniques reflected different characteristics of the residual bubble distribution: bubble size and the speed of dissolution (Color Doppler), the degree of change in bubble distribution from one HIFU pulse to the next (Interleaving Doppler) and the magnitude of the bubble nonlinear response (Pulse Inversion Doppler). Therefore, the sensitivities of the three techniques were likely to be different and were measured, similarly to the PCD, in terms of the threshold for 50% probability of observation of a cavitation event (see Section II B). A cavitation event in this case was considered observed if color was displayed on top of the B-mode image.

In the Color Doppler sequence, the color images were not displayed until HIFU focal peak negative pressure reached 3.1 MPa (FIGS. 17(a) and 17(b)). The Interleaving Doppler sequence appeared to have the lowest threshold compared to most other techniques −1.9 MPa (FIGS. 17(c) and 17(d)), and the displayed distribution was larger in size than in the other sequences at the same HIFU power level. The threshold in the Pulse Inversion Doppler sequence was similar to that in the Color Doppler sequence: 3.1 MPa (FIGS. 17(e) and 17(f)).

The sensitivities of most of the Doppler techniques were compared to that of the PCD and the high speed photography, and are summarized in the table below. The comparison was performed separately for the Interleaving Doppler to account for the smaller HIFU pulse duration used in this technique. The accuracy of the thresholds was mostly determined by the step size by which the peak negative focal HIFU pressure was increased −0.5 MPa. As seen, all of the Doppler techniques appeared substantially more sensitive than other methods.

| | Techniques | | | | | | |
|---|---|---|---|---|---|---|---|
| | Single 1-ms HIFU pulse | | | Twelve 200-us HIFU pulses | | | |
| | PCD | High Speed photography | Color Doppler | Pulse Inversion Doppler | PCD | High Speed photography | Interleaving Doppler |
| Peak-rarefractional pressure at 50% probability of cavitation event (MPa) | 4.6 | 5.1 | 3.1 | 3.1 | 5.1 | 5.6 | 1.9 |

Discussion

In this work, we investigated the feasibility and sensitivity of three different Doppler techniques in detection of pHIFU induced cavitation bubbles: Color Doppler, Pulse Inversion Doppler and Interleaving Doppler. These techniques were found to be not only more sensitive than conventional PCD or high speed photography, but also complementary to each other, i.e. providing different information on the bubble distribution.

In the Interleaving Doppler, the Doppler signal amplitude fluctuates over slow time (i.e. from one HIFU pulse to the next) because each HIFU pulse produces a different bubble distribution. It can therefore be interpreted as sensitive to the mere presence of bubbles, not necessarily bubble activity, and was found to be the most sensitive among the considered techniques. In its concept, the Interleaving Doppler is similar to Doppler decorrelation algorithm[11,12], which measures the decorrelation of backscattered signals from the UCAs before and after they are disrupted by a more intense pulse. The difference from our case is that the intense pulse is the bubble-producing HIFU pulse, and more than two Doppler pulses are used.

The Doppler signal in the Color Doppler mode originates from the change in the size of the bubbles as they dissolve rapidly after HIFU is turned off. The signal is therefore representative primarily of the bubble size, but also of the elastic properties of the medium around the bubble, because it would influence the dissolution speed. The Pulse Inversion Doppler was found to have similar sensitivity to Color Doppler, and is an indicator of the strength of the bubble's nonlinear response to the Doppler ensemble pulses. This response is, in turn, dictated by the bubble size and the medium properties. However, Pulse Inversion Doppler has an important advantage over Color Doppler in the in vivo implementation—it is only sensitive to the nonlinear scatterers, and is not cluttered by the linear signal component reflecting body motion or blood circulation.

Figure 18:
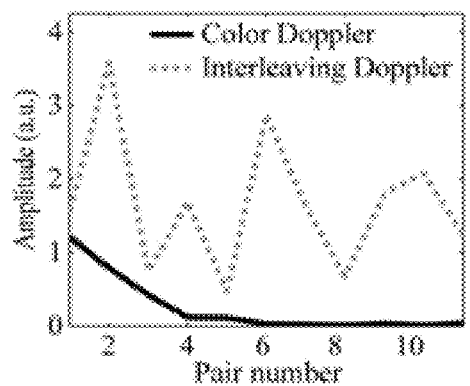
FIG. 18 depicts an example representation of a measurement associated with reflection waves in accordance with one or more example embodiments.

In most pulsing sequences used in this work, 12 Doppler pulses per ensemble were used, primarily because this is the default number for many clinical ultrasound machines. However, this number may potentially be reduced to increase imaging speed, depending on the bubble dissolution time (for Color Doppler and Pulse Inversion Doppler) and the degree of changes in bubble distribution between HIFU pulses. In order to find out the optimal number of pulses in the Doppler ensemble, the amplitude of autocorrelation function between two consecutive RF pulses was plotted along slow time and compared between different pulse sequences (FIG. 18). As seen, the autocorrelation amplitude drops very rapidly in the Color Doppler case and hardly changes after the 6$^{th}$ pulse of the ensemble. Therefore, the number of pulses can be reduced in this case without the loss of signal strength. In the Interleaving Doppler case, the autocorrelation amplitude changes randomly across the pulse pairs, therefore, the more pulses are delivered, the stronger the Doppler signal. The number of pulses in the ensemble can thus be adjusted based on the needs in a particular situation.

In this work, most or all of the Doppler methods were implemented in a flash mode, because the cavitation bubbles are very transient, and transmitting multiple beams or waves at multiple angles would not be rapid enough to capture these bubbles. The flash mode is known to provide relatively poor spatial resolution[13,14] that was not critical in this pilot study, but would certainly be unacceptable in a clinical setting. However, since the number of pulses in a Doppler ensemble can be substantially reduced, it is potentially feasible to utilize multiple transmit beams or incident angles within the same imaging time, and enhance the image resolution.

As the Interleaving Doppler and Pulse Inversion Doppler provide complementary information about the cavitation bubbles, they can be combined into a single method by using more complex pulsing sequences with multiple HIFU pulses, followed by multiple Doppler ensemble pulses with interchanging polarities. This method, that we term "Bubble Doppler" would quantify the bubble nonlinearity and map the bubble presence at the same time, and is likely to provide superior sensitivity compared to PCD methods. It would also be readily translatable for clinical use, because it uses a commercially available imaging probe, which can be incorporated into a HIFU system.

CONCLUSIONS

In this manuscript, the methods for pHIFU induced microbubbles detection were studied. Color Doppler imaging shows the decrease in bubbles sizes after HIFU pulse. Pulse inversion allows quantifying the nonlinearity of the bubbles. Interleaving Doppler may be one of the most sensitive to the presence of bubbles among numerous techniques.

The combination of these techniques is likely to be beneficial for imaging of bubble location and characterization of bubbles nonlinearity. In summary, a new ultrasound imaging protocol was proposed to detect microbubbles induced by pHIFU using a modification of Doppler pulses sequences. This imaging modality was shown to provide the sensitivity superior to that of existing cavitation detection methods, and at the same time allows to spatially resolving bubble location, as inherent to the conventional Doppler imaging.

REFERENCES

[1] V. A. Khokhlova, M. R. Bailey, J. A. Reed, B. W. Cunitz, P. J. Kaczkowski, and L. A. Crum, "Effects of nonlinear propagation, cavitation, and boiling in lesion formation by high intensity focused ultrasound in a gel phantom," *J. Acoust. Soc. Am.*, vol. 119, p. 1834,2006.

[2] C. Lafon, V. Zderic, M. L. Noble, J. C. Yuen, P. J. Kaczkowski, O. A. Sapozhnikov, F. Chavrier, L. A. Crum, and S. Vaezy, "Gel phantom for use in high-intensity focused ultrasound dosimetry.," *Ultrasound Med. Biol.*, vol. 31, pp. 1383-1389, October 2005.

[3] T. D. Khokhlova, M. S. Canney, V. A. Khokhlova, O. A. Sapozhnikov, L. A. Crum, and M. R. Bailey, "Controlled tissue emulsification produced by high intensity focused ultrasound shock waves and millisecond boiling," *J. Acoust. Soc. Am.*, vol. 130, pp. 3498-3510, 2011.

[4] T. Li, H. Chen, T. Khokhlova, Y.-N. Wang, W. Kreider, X. He, and J. H. Hwang, "Passive Cavitation Detection during Pulsed HIFU Exposures of Ex Vivo Tissues and In Vivo Mouse Pancreatic Tumors.," *Ultrasound Med. Biol.*, March 2014.

[5] R. Daigle, "Sequence programming manual." Verasonics, pp. 64-65, 2011.

[6] W. Lu, O. A. Sapozhnikov, M. R. Bailey, P. J. Kaczkowski, and L. A. Crum, "Evidence for Trapped Surface Bubbles as the Cause for the Twinkling Artifact in Ultrasound Imaging," *Ultrasound Med. Biol.*, vol. 39, no. 6, pp. 1026-1038, 2013.

[7] O. A. Sapozhnikov, T. Li, T. D. Khokhlova, M. O'Donnell, V. A. Khokhlova, and J. H. Hwang, "No Title," in *A new active cavitation mapping technique for pulsed hifu applications—bubble doppler*, 2014.

[8] D. H. Simpson, C. T. Chin, and P. N. Burns, "Pulse inversion Doppler: a new method for detecting nonlinear echoes from microbubble contrast agents.," *Ferroelectr. Freq. Control*, vol. 61, no. 1, pp. 102-19, *IEEE Trans. Ultrason. Ferroelectr. Freq. Control*, vol. 46, no. 2, pp. 372-382,1999.

[9] C. Kasai, K. Namekawa, a. Koyano, and R. Omoto, "Real-Time Two-Dimensional Blood Flow Imaging Using an Autocorrelation Technique," *IEEE Trans. Sonics Ultrason.*, vol. 32, no. 3, pp. 458-464, May 1985.

[10] D. H. Evans and W. N. McDicken, *Doppler Ultrasound—physics, instrumentation and clinical applications*. 2000.

[11] P. Frinking, "Multi-pulse ultrasound contrast imaging based on a decorrelation detection strategy," *IEEE Ultrason. Symp. Proc.*, vol. 2, pp. 1787-1790, 1998.

[12] J. M. Rubin, T. A. Tuthill, and J. B. Fowlkes, "Volume flow measurement using doppler and grey-scale decorrelation," *Ultrasound Med. Biol.*, vol. 27, no. 1, pp. 101-109, 2001.

[13] G. Montaldo, M. Tanter, J. Bercoff, N. Benech, and M. Fink, "Coherent plane-wave compounding for very high frame rate ultrasonography and transient elastography.," *IEEE Trans. Ultrason. Ferroelectr. Freq. Control*, vol. 56, no. 3, pp. 489-506, 2009.

[14] M. Tanter and M. Fink, "Ultrafast imaging in biomedical ultrasound.," *IEEE Trans. Ultrason.* 2014.

8. CONCLUSION

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying Figures. In the Figures, similar symbols typically identify similar components, unless context dictates otherwise. It will be readily understood that the aspects of the present disclosure, as generally described herein, and illustrated in the Figures, can be arranged, substituted, combined, separated, and designed in a wide variety of different configurations, all of which are explicitly contemplated herein.

With respect to any or all of the diagrams, scenarios, and flow charts in the Figures and as discussed herein, each block and/or communication can represent a processing of information and/or a transmission of information in accordance with example embodiments. Alternative embodiments are included within the scope of these example embodiments. In these alternative embodiments, for example, functions described as blocks, transmissions, communications, requests, responses, and/or messages can be executed out of order from that shown or discussed, including substantially concurrent or in reverse order, depending on the functionality involved. Further, more or fewer blocks and/or functions can be used with any of the ladder diagrams, scenarios, and flow charts discussed herein, and these ladder diagrams, scenarios, and flow charts can be combined with one another, in part or in whole.

A block that represents a processing of information can correspond to circuitry that can be configured to perform the specific logical functions of a herein-described method or technique. Alternatively or additionally, a block that represents a processing of information can correspond to a module, a segment, or a portion of program code (including related data). The program code can include one or more instructions executable by a processor for implementing specific logical functions or actions in the method or technique. The program code and/or related data can be stored on any type of computer readable medium such as a storage device including a disk or hard drive or other storage medium.

The computer readable medium can also include physical and/or non-transitory computer readable media such as computer-readable media that stores data for short periods of time like register memory, processor cache, and random access memory (RAM). The computer readable media can also include physical and/or non-transitory computer readable media that stores program code and/or data for longer periods of time, such as secondary or persistent long term storage, like read only memory (ROM), optical or magnetic disks, compact-disc read only memory (CD-ROM), for example. The computer readable media can also be any other volatile or non-volatile storage systems. A computer readable medium can be considered a computer readable storage medium, for example, or a tangible storage device.

Moreover, a block that represents one or more information transmissions can correspond to information transmissions between software and/or hardware modules in the same physical device. However, other information transmissions can be between software modules and/or hardware modules in different physical devices.

The particular arrangements shown in the Figures should not be viewed as limiting. It should be understood that other embodiments can include more or less of each element shown in a given Figure. Further, some of the illustrated elements can be combined or omitted. Yet further, an example embodiment can include elements that are not illustrated in the Figures.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A method for imaging a cavitation bubble comprising:
producing one or more vibratory pulses that form a cavitation bubble in a medium;
producing a plurality of detection pulses that are directed toward the formed cavitation bubble;
receiving a plurality of reflection pulses that correspond respectively to the plurality of detection pulses, wherein the plurality of received reflection pulses are reflected from the formed cavitation bubble;
comparing a first reflection pulse of the plurality of reflection pulses to one or more other reflection pulses of the plurality of reflection pulses to identify a change in one or more characteristics of the formed cavitation bubble; and
based on the identified change, generating an image of the formed cavitation bubble using a computing device;
wherein the one or more vibratory pulses comprise a high-intensity focused ultrasound (HIFU) wave, and wherein the HIFU wave is characterized by at least one of the following: an oscillation frequency within a range of approximately 0.1 MHz to 10 MHz, a peak pressure induced in the medium within a range of approximately 2 MPa to 150 MPa, a pulse repetition frequency within a range of approximately 1 Hz to 20 kHz, or a pulse duration within a range of 10 microseconds to 100 milliseconds;
wherein at least one vibratory pulse of the one or more vibratory pulses is produced prior to production of the plurality of detection pulses;
wherein comparing the first reflection pulse to the one or more other reflection pulses comprises determining a difference between an oscillation frequency of the first reflection pulse and an oscillation frequency of the one or more other reflection pulses; and
wherein the plurality of detection pulses comprise:
one or more first detection pulses; and
one or more second detection pulses,
wherein each of the one or more first detection pulses has a waveform that is inverted with respect to a respective detection pulse of the one or more second detection pulses, and
wherein each of the one or more first detection pulses is followed by a respective detection pulse of the second one or more detection pulses.

2. The method of claim 1, wherein the plurality of detection pulses comprise at least one of the following: (a) one or more radio-frequency pulses, (b) one or more microwave pulses, (c) one or more optical pulses, or (d) one or more acoustic pulses.

3. The method of claim 1, wherein the medium comprises at least one of the following: (a) bodily tissue, (b) cancer tissue, (c) water, (d) blood, (e) urine, (f) bile, (g) mucus, (h) pus, (i) semen, (j) saliva, (k) pericardial fluid, (l) peritoneal fluid, (m) pleural fluid, (n) gastric fluid, (o) stool, (p) synovial fluid, (q) cerebrospinal fluid, (r) lymph, or (s) exudate.

4. The method of claim 1, wherein the formed cavitation bubble is associated with an object in the medium, wherein the medium is present within a subject, and wherein the object comprises at least one of the following: (a) a urinary tract stone, (b) a kidney stone, (c) a ureter stone, (d) a bladder stone, (e) a urethra stone, (f) a prostate stone, (g) a salivary stone, (h) a gallbladder stone, (i) a gall stone, (j) a bile duct, (k) a blood clot, (l) cerumen, (m) a calcification, (n) a calcified plaque, (o) an atherosclerotic plaque, (p) a struvite, (q) calcium oxalate monohydrate (COM), (r) a cystine, (s) a tonsil stone, (t) an artificial object, or (u) an object introduced inside the subject's body.

5. The method of claim 1, wherein the plurality of detection pulses comprise one or more acoustic pulses, and wherein the one or more acoustic pulses are characterized by at least one of the following: an oscillation frequency within a range of approximately 1 MHz to 40 MHz, a pulse repetition frequency within a range of approximately 1 Hz to 20 kHz, and a number of cycles within a range of approximately 1 to 10 cycles.

6. A non-transitory computer-readable medium storing program instructions that, when executed by a processor of an ultrasound device, cause the ultrasound device to perform functions comprising:
producing one or more vibratory pulses that form a cavitation bubble in a medium;
producing a plurality of detection pulses that are directed toward the formed cavitation bubble;
receiving a plurality of reflection pulses that correspond respectively to the plurality of detection pulses, wherein the plurality of reflection pulses are reflected from the formed cavitation bubble;
comparing a first reflection pulse of the plurality of reflection pulses to one or more other reflection pulses of the plurality of reflection pulses to identify a change in one or more characteristics of the formed cavitation bubble; and
based on the identified change, generating an image of the formed cavitation bubble;
wherein the one or more vibratory pulses comprise a high-intensity focused ultrasound (HIFU) wave, and wherein the HIFU wave is characterized by at least one of the following: an oscillation frequency within a range of approximately 0.1 MHz to 10 MHz, a peak pressure induced in the medium within a range of approximately 2 MPa to 150 MPa, a pulse repetition frequency within a range of approximately 1 Hz to 20 kHz, or a pulse duration within a range of 10 microseconds to 100 milliseconds;
wherein at least one vibratory pulse of the one or more vibratory pulses is produced prior to production of the plurality of detection pulses;
wherein comparing the first reflection pulse to the one or more other reflection pulses comprises determining a difference between an oscillation frequency of the first reflection pulse and an oscillation frequency of the one or more other reflection pulses; and
wherein the plurality of detection pulses comprise:
one or more first detection pulses; and
one or more second detection pulses,
wherein each of the one or more first detection pulses has a waveform that is inverted with respect to a respective detection pulse of the one or more second detection pulses, and wherein each of the one or more first detection pulses is followed by a respective detection pulse of the second one or more detection pulses.

7. An ultrasound device, comprising:
a processor;
a display; and
a non-transitory computer-readable medium storing program instructions that, when executed by the processor, cause the ultrasound device to perform functions comprising:
producing one or more vibratory pulses that form a cavitation bubble in a medium;
producing a plurality of detection pulses that are directed toward the formed cavitation bubble;
receiving a plurality of reflection pulses that correspond respectively to the plurality of detection pulses, wherein the plurality of received reflection pulses are reflected from the formed cavitation bubble;
comparing a first reflection pulse of the plurality of reflection pulses to one or more other reflection pulses of the plurality of reflection pulses to identify a change in one or more characteristics of the formed cavitation bubble; and
based on the identified change, generating an image of the formed cavitation bubble using the display;
wherein the one or more vibratory pulses comprise a high-intensity focused ultrasound (HIFU) wave, and wherein the HIFU wave is characterized by at least one of the following: an oscillation frequency within a range of approximately 0.1 MHz to 10 MHz, a peak pressure induced in the medium within a range of approximately 2 MPa to 150 MPa, a pulse repetition frequency within a range of approximately 1 Hz to 20 kHz, or a pulse duration within a range of 10 microseconds to 100 milliseconds;
wherein at least one vibratory pulse of the one or more vibratory pulses is produced prior to production of the plurality of detection pulses;
wherein comparing the first reflection pulse to the one or more other reflection pulses comprises determining a difference between an oscillation frequency of the first reflection pulse and an oscillation frequency of the one or more other reflection pulses; and
wherein the plurality of detection pulses comprise:
one or more first detection pulses; and
one or more second detection pulses,
wherein each of the one or more first detection pulses has a waveform that is inverted with respect to a respective detection pulse of the one or more second detection pulses, and
wherein each of the one or more first detection pulses is followed by a respective detection pulse of the second one or more detection pulses.

8. A method comprising:
producing one or more vibratory pulses that form a cavitation bubble in a medium located within a subject;
producing a plurality of detection pulses that are directed toward the formed cavitation bubble;
receiving a plurality of reflection pulses that correspond respectively to the plurality of detection pulses, wherein the plurality of received reflection pulses are reflected from the formed cavitation bubble;
comparing a first reflection pulse of the plurality of reflection pulses to one or more other reflection pulses of the plurality of reflection pulses to identify a change in one or more characteristics of the formed cavitation bubble; and
based on the identified change, generating an image of the formed cavitation bubble using a computing device;
wherein the one or more vibratory pulses comprise a high-intensity focused ultrasound (HIFU) wave, and wherein the HIFU wave is characterized by at least one of the following: an oscillation frequency within a range of approximately 0.1 MHz to 10 MHz, a peak pressure induced in the medium within a range of approximately 2 MPa to 150 MPa, a pulse repetition frequency within a range of approximately 1 Hz to 20 kHz, or a pulse duration within a range of 10 microseconds to 100 milliseconds;
wherein at least one vibratory pulse of the one or more vibratory pulses is produced prior to production of the plurality of detection pulses;
wherein comparing the first reflection pulse to the one or more other reflection pulses comprises determining a difference between an oscillation frequency of the first reflection pulse and an oscillation frequency of the one or more other reflection pulses; and
wherein the plurality of detection pulses comprise:
one or more first detection pulses; and
one or more second detection pulses,
wherein each of the one or more first detection pulses has a waveform that is inverted with respect to a respective detection pulse of the one or more second detection pulses, and
wherein each of the one or more first detection pulses is followed by a respective detection pulse of the second one or more detection pulses.

9. The method of claim 8, wherein the subject suffers from one or more of: (a) cancer, (b) an orthopedic disorder, or (c) a neurological disorder.

10. The method of claim 8, wherein the one or more vibratory pulses and the plurality of detection pulses are produced using a probe, wherein the probe includes at least one of the following: (a) an unfocused transducer, (b) a focused transducer, or (c) a plurality of transducers forming a phased array.

11. The method of claim 10, wherein a substance is between the probe and the subject, and wherein the substance includes at least one of the following: (a) water, (b) gel, or (c) a flexible container filled with a liquid.

12. The method of claim 8, wherein the method further comprises using the generated image to monitor progress of an ultrasound therapy administered to the subject.

* * * * *